United States Patent [19]

Lakowicz et al.

[11] Patent Number: 5,631,169
[45] Date of Patent: May 20, 1997

[54] FLUORESCENT ENERGY TRANSFER IMMUNOASSAY

[75] Inventors: Joseph R. Lakowicz, 9142 Emerson's Reach, Columbia, Md. 21045; Badri P. Maliwal, Baltimore, Md.; Richard Thompson, 7106 Bristol Rd., Baltimore, Md. 21212; Alvydas Ozinskas, Dayton, Md.

[73] Assignees: Joseph R. Lakowicz, Ellicott City; Richard Thompson, Baltimore, both of Md.

[21] Appl. No.: 183,238

[22] Filed: Jan. 19, 1994

Related U.S. Application Data

[63] Continuation of Ser. No. 822,233, Jan. 27, 1992, abandoned.

[51] Int. Cl.[6] .................................................. G01N 33/533
[52] U.S. Cl. .................... 436/537; 436/536; 436/518; 436/546; 436/172; 436/800; 422/82.07; 422/82.08; 422/82.09
[58] Field of Search .................................. 436/172, 518, 436/546, 800, 536, 537; 435/968; 422/82.07, 82.08, 82.09

[56] References Cited

U.S. PATENT DOCUMENTS

| | | | |
|---|---|---|---|
| 4,174,384 | 11/1979 | Ullman | 436/537 |
| 4,822,733 | 4/1989 | Morrison | 435/6 |

FOREIGN PATENT DOCUMENTS

| | | |
|---|---|---|
| 0242847 | 4/1987 | European Pat. Off. . |
| 2223096 | 3/1990 | United Kingdom . |
| 8707385 | 5/1987 | WIPO . |

OTHER PUBLICATIONS

Ozinskas et al, Anal. Biochem. 213 pp. 264–270 (1993) "Homogenous Model Immunoassay of Thyroxine by Phase–Modulation Fluorescence Spectroscopy".

Lovgren et al in *Luminescence Immunoassay and Molecular Application* CRC Press 1990 pp. 233–253.

Lakowicz *Principles of Fluorescence Spectroscopy* (1983) Plenum Press Chapter 3 pp. 51–93.

Lakowicz et al Biophysical Chemistry 21 (1985) 61–78.

Soini et al CRC Critical Reviews in Anal. Chem. 18 #2 (1987) pp. 105–154.

Hemmila Clin. Chem 31/3, 359–370 (1985).

Analytical Chemistry, vol. 56 (No. 13) Nov. 1984, "Phase Resolved Fluorescence Spectroscopy"L. B. McGown et al.

Cytometry, vol. 10, 1989, pp. 11–19; "Cyanine Dye Labeling Reagents Containing Isothiocyanate Groups[1]"R. B. Mujumdar et al.

Dyes and Pigments, vol. 17, 1991, pp. 19–27; "Synthesis and Characterization of 1,3–Bis(2–dialkylamino– 5–thienyl)– substituted Squaraines . . . "Dietmar Keil.

(List continued on next page.)

*Primary Examiner*—Lora M. Green
*Attorney, Agent, or Firm*—Rothwell, Figg, Ernst & Kurz

[57] ABSTRACT

A fluorometric luminescence immunoassay method includes forming a sample by exposing a first immune reaction reactant to a second immune reaction reactant capable of reacting with the first reactant, one of the first and second immune reaction reactants being labelled with a photoluminescent energy transfer donor and the other being labelled with a photoluminescent energy transfer acceptor complementary to the photoluminescent donor. At least the photoluminescent donor has the property of photoluminescence, and the photoluminescent donor and acceptor are chosen so that when the first immune reaction reactant reacts with the second immune reaction reactant, the donor and the acceptor are capable of interacting to produce a detectable luminescence lifetime change. The sample is excited with radiation, and the resulting emission is detected. The apparent luminescent lifetime is then calculated to determine the presence of a reaction product of the first and second immune reaction reactants.

22 Claims, 8 Drawing Sheets

OTHER PUBLICATIONS

Clinical Chemistry, vol. 25 (No. 3) 1979, pp. 353–361; "Fluoroimmunoassay: Present Status and Key Problems" Erkki Soini et al.

Laser Focus World, vol. 28, (No. 5), May 1992, pp. 60–80; "Fluorescence Lifetime Sensing" J. R. Lakowicz.

Analytical Chemistry, vol. 59, 1987, pp. 423–427; "Homogeneous Immunochemical Technique for Determination of Human Lactoferrin Using Excitation Transfer and Phase–Resolved Fluorometry[1]" K. Nithipatikom et al.

FLUORESCENT ENERGY TRANSFER IMMUNOASSAY

This application is a continuation of U.S. application Ser. No. 07/822,233 filed Jan. 27, 1992 now abandoned.

FIELD OF THE INVENTION

The present invention is directed to a method for an optical immunoassay and, more particularly, to a method in which immune reaction reactants are separately labelled with a photoluminescent energy transfer donor and acceptor. The energy transfer resulting when the donor and acceptor are brought into close proximity to each other when the immune reaction occurs produces a detectable luminescence lifetime change.

BACKGROUND OF THE INVENTION

Immunoassays have been based on a variety of methods, including visual and radioactivity determinations. It also is known to optically evaluate immune reactions by using fluorescence intensity measurements. Although fluorescence intensity measurements are desirable in their simplicity, the usefulness of this technique is limited due to problems such as source fluctuations due to noise, drift and the like, fluorophore bleaching, and background fluorescence. Further, if the media is turbid or colored, the intensity measurements will be greatly affected. Moreover, since intensity is a linear product of numerous factors, such as the amount of fluorophore in each state, the excitation intensity, the excitation and emission bandpass, the wavelength sensitivity of the detector, and the like, a complex set of calibration curves must be used to correct for these factors. And finally, a change in the intensity of the probe does not necessarily occur upon binding of antigen and antibody. Thus, while fluorometric intensity measurements can provide useful and highly sensitive results under certain circumstances, they suffer from limited usefulness due to the problems outlined above.

SUMMARY OF THE INVENTION

The present invention provides a method in which a change in the apparent luminescence lifetime of a photoluminescent energy transfer donor or acceptor may be correlated with an immune reaction product. In the context of the present invention, an immune reaction can be considered to occur when there is a specific, non-covalent binding of an antigen with at least one cognizant antibody. The photoluminescent donor and acceptor are carried on immune reaction reactants, so that when an immune reaction occurs, the donor and acceptor can interact, i.e. so that energy transfer occurs between the donor and acceptor, which in turn results in a detectable luminescence lifetime change. By measuring lifetimes, the problems associated with intensity measurements are avoided. The apparent lifetime can be measured by phase-modulation fluorometry or time-resolved fluorometry. By use of this method, immunoassay can be carried out in vivo, in vitro or in situ. Relatively long wavelength fluorescent labels are particularly useful.

DETAILED DESCRIPTION OF THE PREFERRED EMBODIMENTS

Figure 1:
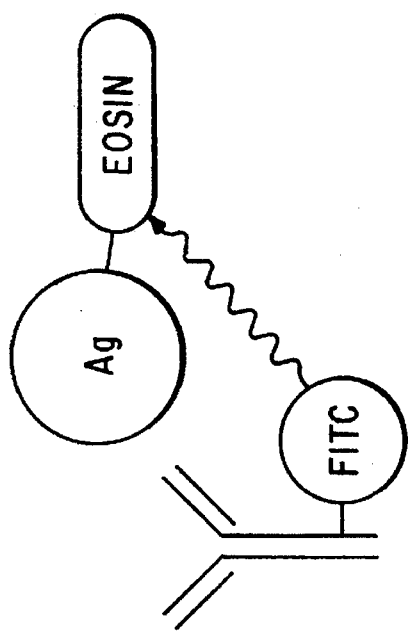
FIGS. 1 and 2 are schematic representations of immune reactions in accordance with a preferred embodiment of the present invention.

The method of the present invention is capable of determining and quantifying the binding reactions used in immunoassay. In the present method, the reactants of the immune reaction are labelled with a photoluminescent energy transfer donor and acceptor, with at least the donor being photoluminescent. The immune reaction of the labelled reactants brings the donor and acceptor into close proximity so that when the reaction product is excited with radiation, energy transfer occurs between the donor and acceptor, which results in a detectable luminescence lifetime change. Anisotropy or polarization and increased or decreased susceptibility to collisional quenchers are properties which also can be used to detect the lifetime change due to energy transfer. The amount of the reaction product, and thus concentration of either of the reactants, or of a competing reactant in a competitive assay, can be determined also. The present method can be used with a variety of immune reactions, including competitive or non-competitive reactions, and including simple antigen-antibody reactions or various sandwich-type assays. The antigen and/or antibody can be provided with more than one donor or acceptor or label.

The term "sample" is used broadly herein to refer to the immunoassay system in which the immune reaction reactants, e.g. antigen and antibody, are allowed to react. This can include standard laboratory environments such as polymeric supports to which one reactant is bound and in which the second reactant is supplied to the support in solution or suspension. This can include liquid samples and/or suspensions, including blood, urine and secretions. It can also refer to a patient in the case of in vivo testing, which is facilitated by the present invention.

The method of the invention further includes exciting the sample with radiation from any suitable radiation source, such as a continuous wave (CW) laser, electroluminescent lamp, arc lamp, light-emitting diode or a laser diode or the like. Light sources particularly suitable for use in the methods of the present invention include green and red helium-neon lasers, helium-cadmium lasers, a Ti-sapphire laser, an argon ion or Nd:YAG laser synch-pumping a dye laser, and red and infrared laser diodes.

In a preferred embodiment, the intensity of the excitation radiation is modulated at a particular modulation frequency, e.g., sinusoidally, and the lifetime determined using known phase-modulation, i.e., frequency-domain, techniques.

Alternatively, a pulsed radiation source such as a square wave light source may be used, and the lifetime of the sample determined using known time-resolved methods. Both phase-modulation and time-resolved fluorometry methods are well known in the prior art, see Lakowicz, *Principles of Fluorescence Spectroscopy*, Plenum Press, 1983, Chapter 3. However, current instrumentation renders the phase-modulation method more expedient. See Lakowicz in *Luminescence Techniques in Chemical and Biochemical Analyses*, pp. 141–177, Baeyers, (Keukeleire and Kurkidis, Eds.), 1991, Marcel-Dekker, Inc.; Berndt, Gryczynski and Lakowicz, *Reviews of Scientific Instrumentation* 1990, 61, pp. 1816–1820; Berndt and Lakowicz, *Analytical Biochemistry* 1991, in press. For the sake of conciseness, only the phase-modulation method will be discussed further herein, but it is understood that these same principles generally apply to time-resolved measurements.

When the sample is excited with radiation whose intensity is modulated, for example, in a sinusoidal manner, the time lag between absorption and emission causes the emission to be delayed in phase and demodulated relative to the excitation radiation. The phase shift and the corresponding demodulation factor m can be measured and used to calculate the photoluminescent lifetime based on well known formulae. See, Lakowicz, *Principles of Fluorescence Spectroscopy*, supra. In the present invention, a phase angle difference of about 45 degrees is especially desirable, because if the angle is significantly larger or smaller the accuracy and dynamic range are reduced.

In accordance with the present invention, energy transfer occurs between the photoluminescent energy transfer donor and the photoluminescent energy transfer acceptor, with at least the donor being photoluminescent. Energy transfer between the donor and acceptor causes a change in the fluorescence lifetime corresponding to the presence of the immune reaction. The efficiency of the energy transfer depends on the quantum yield of the donor, the overlapping of the emission spectrum of the donor with the absorption spectrum of the acceptor, and the relative distance and orientation between the donor and the acceptor.

The donors used in the present invention should exhibit good quantum yield, lifetime and extinction coefficient, resistance to collisional quenching and bleaching, and should preferably be water-soluble and easily conjugated to the immune reaction reactant. Particularly desirable are donors which show absorbance and emission in the red and near infrared range, which will be useful in whole blood and living tissue analysis, since they will be free from problems associated with scattering and background fluorescence. Advantageously, relatively inexpensive, modestly powerful and readily-modulated laser diodes can be used as the light source for such donors. The donor will preferably have a lifetime of about 0.1 nanosecond to 1 second, with typical donors being on the order of 1 to 30 nanoseconds, more preferably about 5 ns. Short lived donors will be about 0.1 nanosecond and higher, long-lived donors about 30 to 400 nanoseconds, and lanthanides up to 1 second.

Examples of such donors include cyanines, oxazines, thiazines, porphyrins, phthalocyanines, fluorescent infrared-emitting polynuclear aromatic hydrocarbons such as violanthrones, phycobtliproteins, maleimides, sulfhydryls, isothiocyanates, succinimidyl esters, carbodiimides, sulfonyl chlorides, haloacetyl derivatives, near IR squaraine dyes for example as shown in *Dyes and Pigments*, 17, pp. 19–27 (1991), and organo-metallic complexes such as the ruthenium and lanthanide complexes of U.S. Pat. Nos. 4,745,076 and 4,670,572, the disclosures of which are incorporated herein by reference. The lanthanide complexes have the advantage of not being quenched by oxygen, and the long lifetimes may allow easy suppression of the autofluorescence of biological samples. Specific materials include fluorescein isothiocyanate (especially fluorescein-5-isothiocyanate), dichlorotriazinylaminofluorescein, teramethylrhodamine-5-(and -6)-isothiocyanate, 1,3-bis-(2-dialkylamino-5-thienyl)-substituted squaraines, the succinimidyl esters of: 5 (and 6)-carboxyfluorescein; 5 (and 6)-carboxytetramethylrhodamine; and 7-amino-4-methylcoumarin-3-acetic acid,

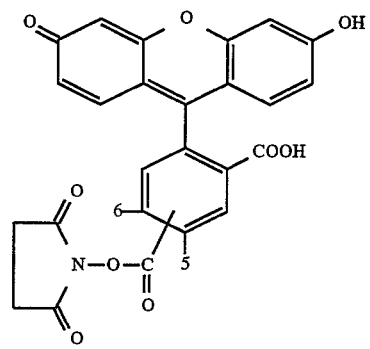

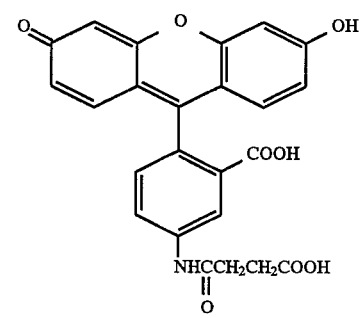

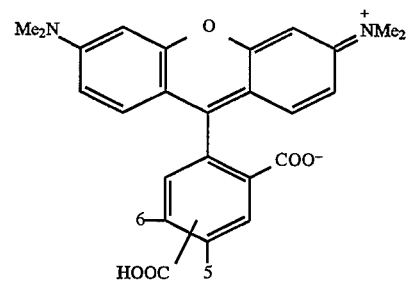

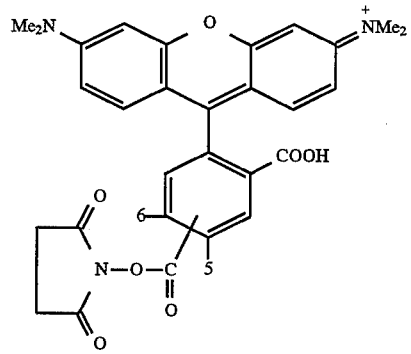

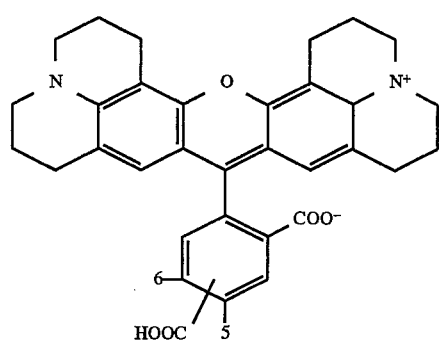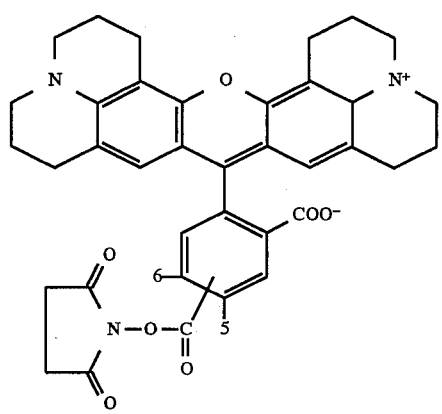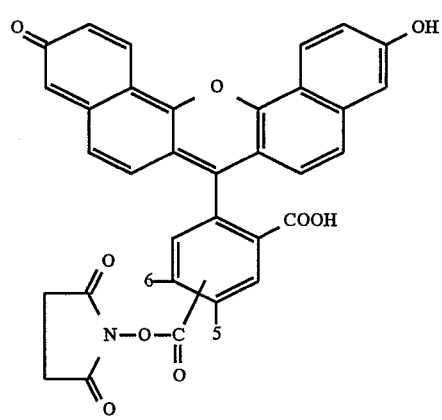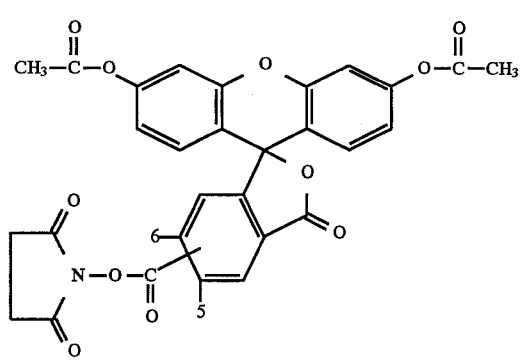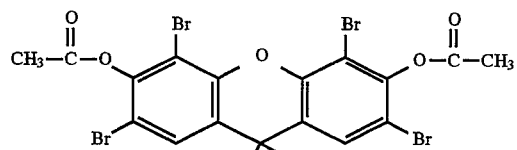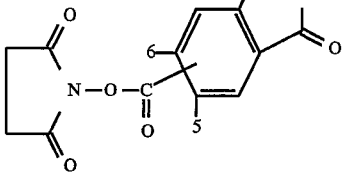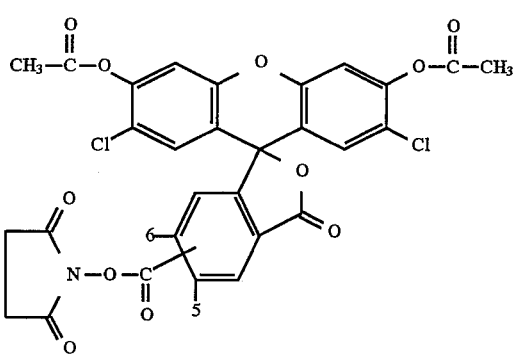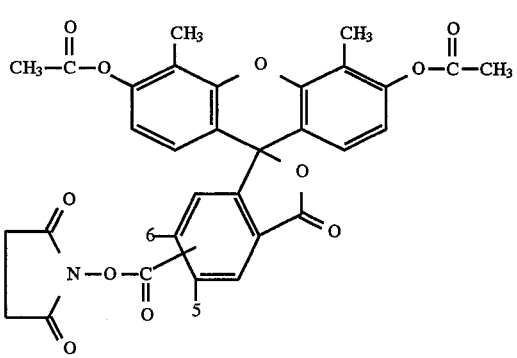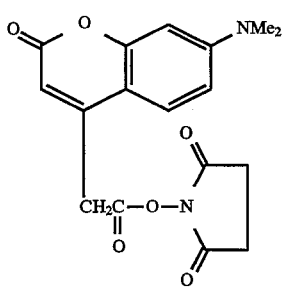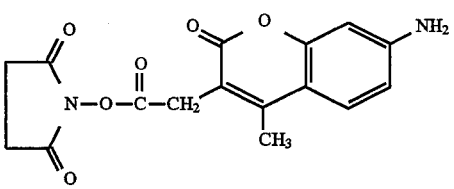

7
-continued
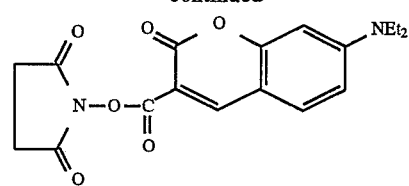
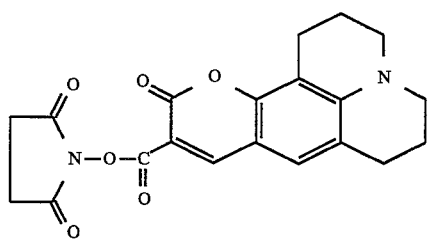
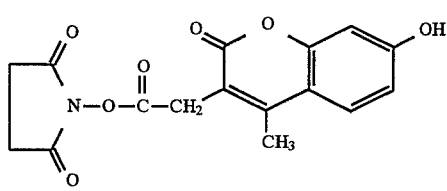
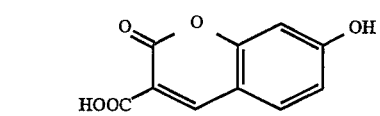
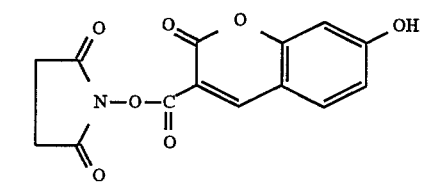
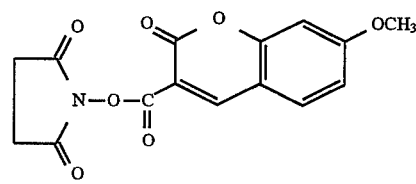
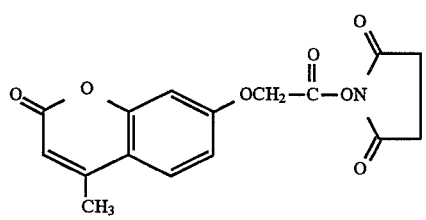
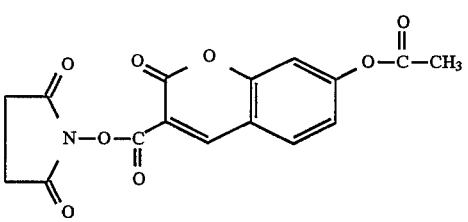
8
-continued
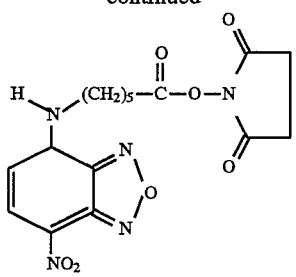
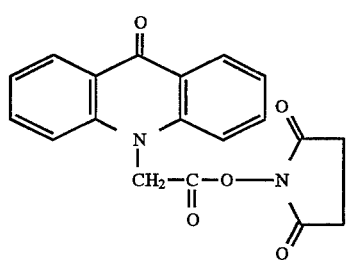
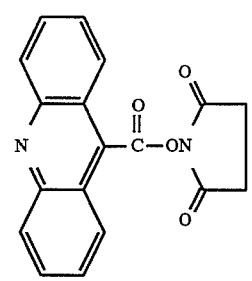
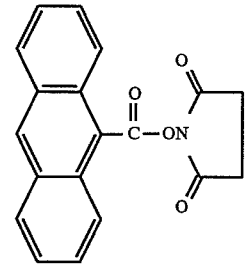
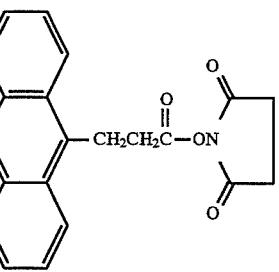
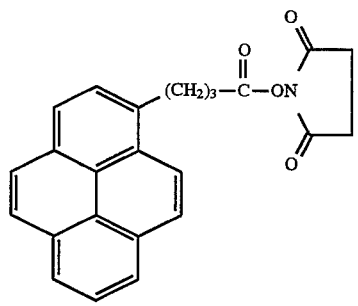

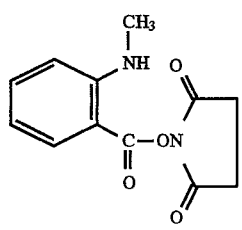
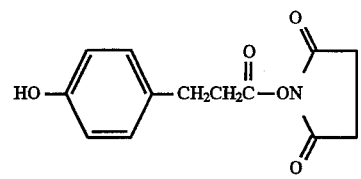
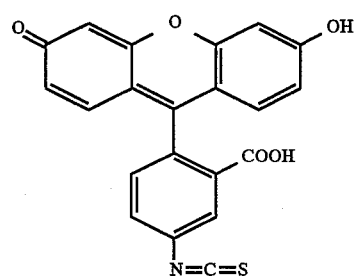
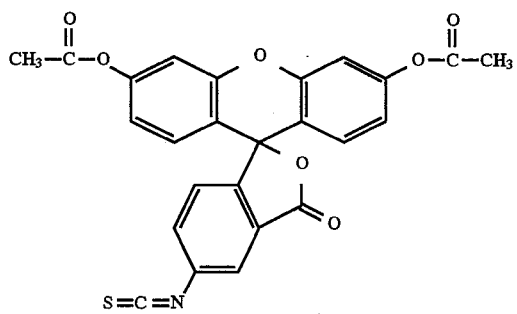
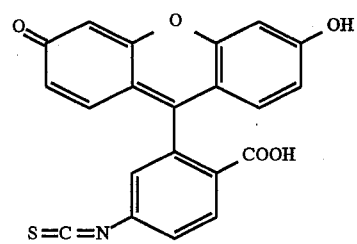
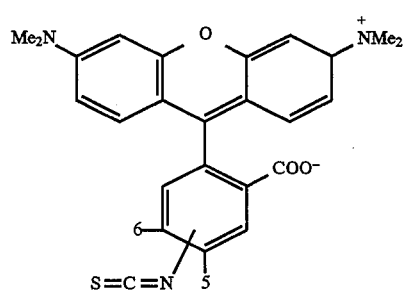
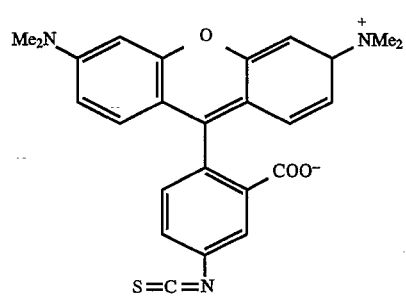
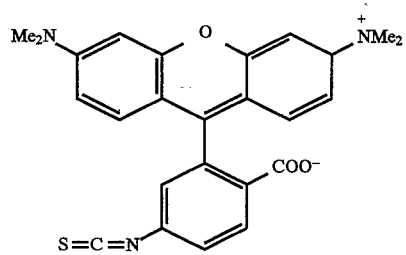
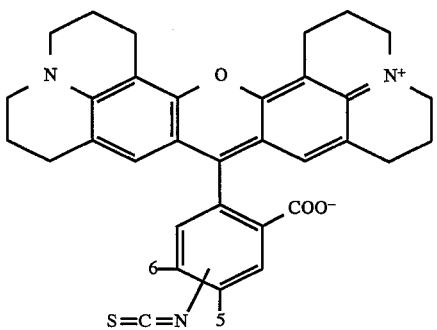
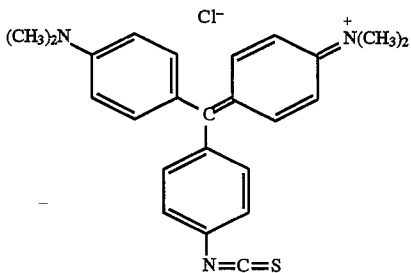
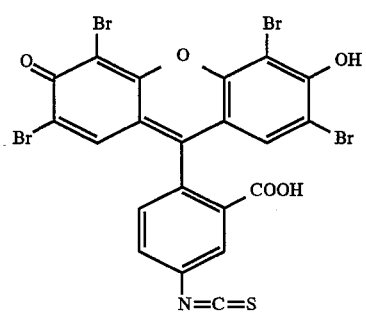

-continued
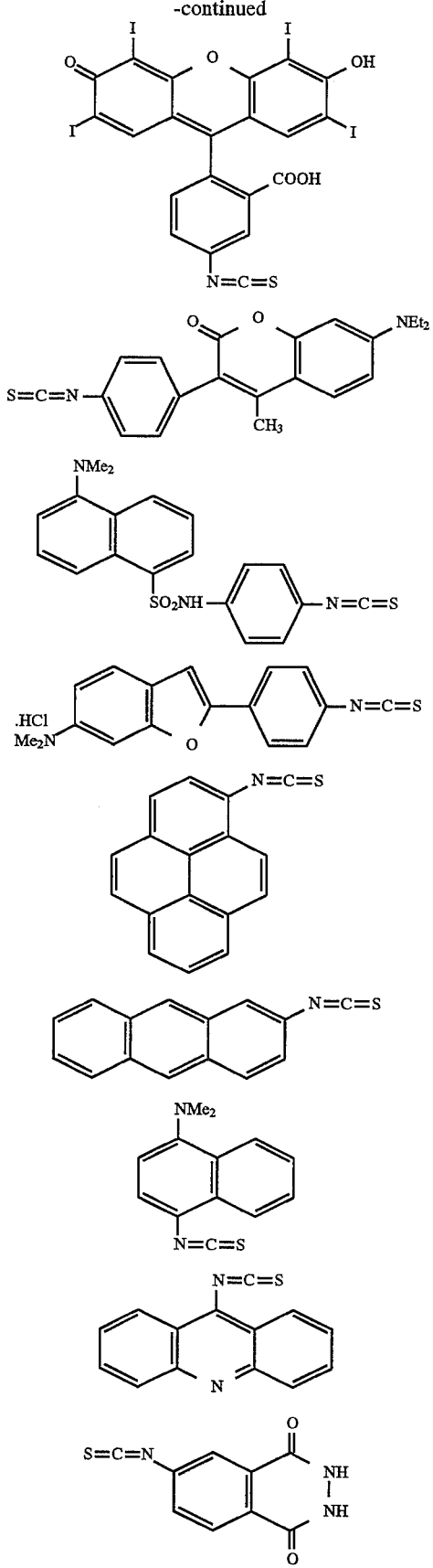
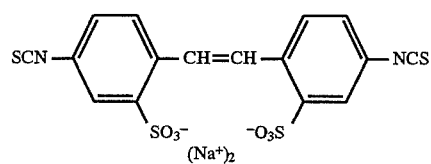
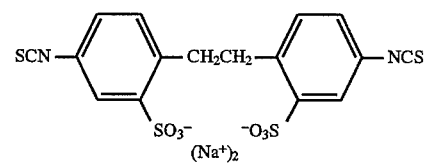
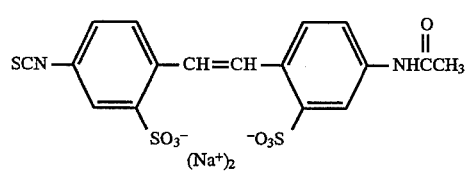
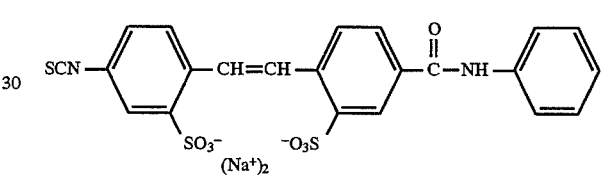
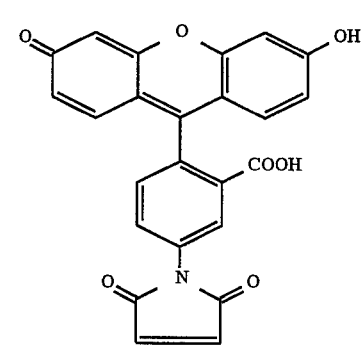
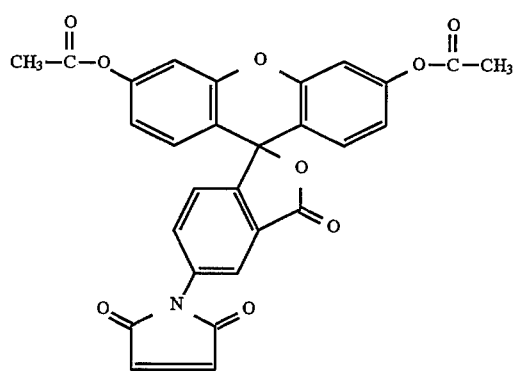

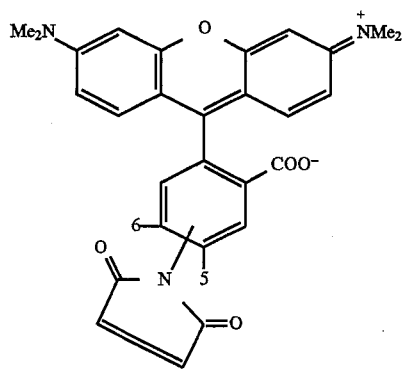
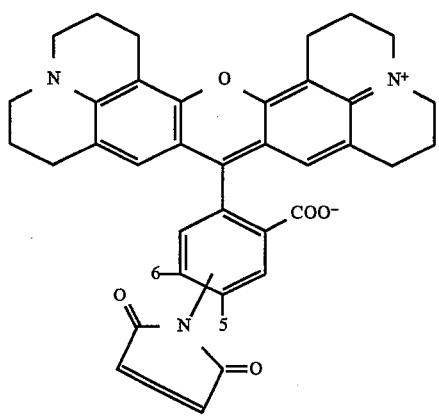
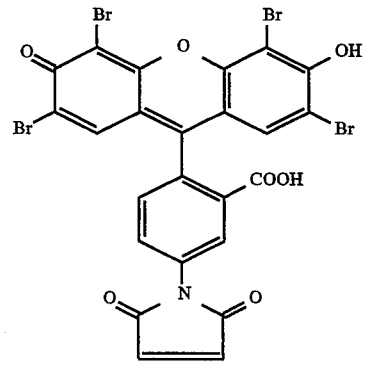
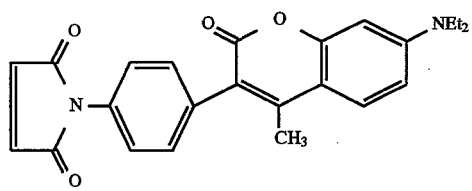
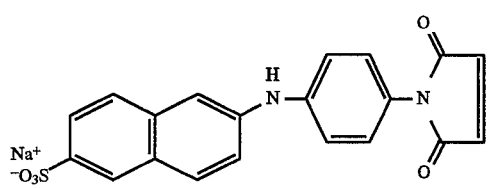
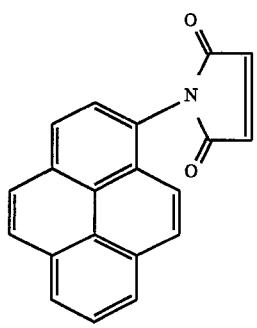
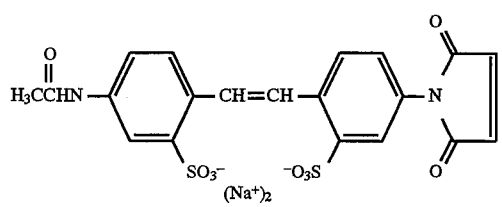
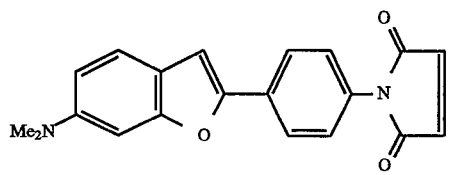
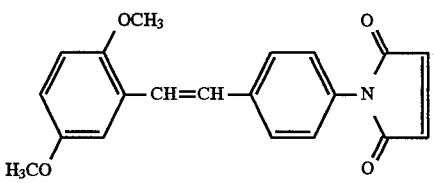
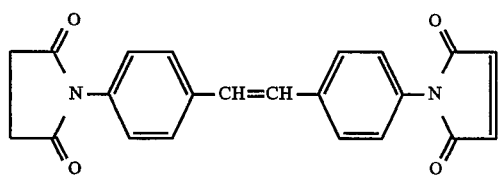
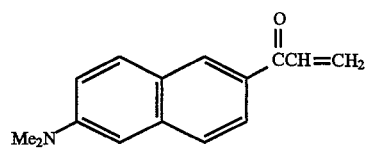
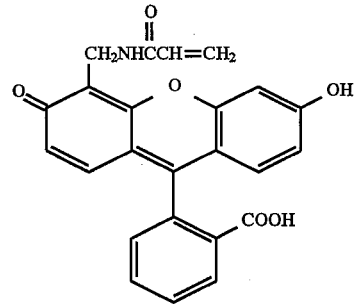

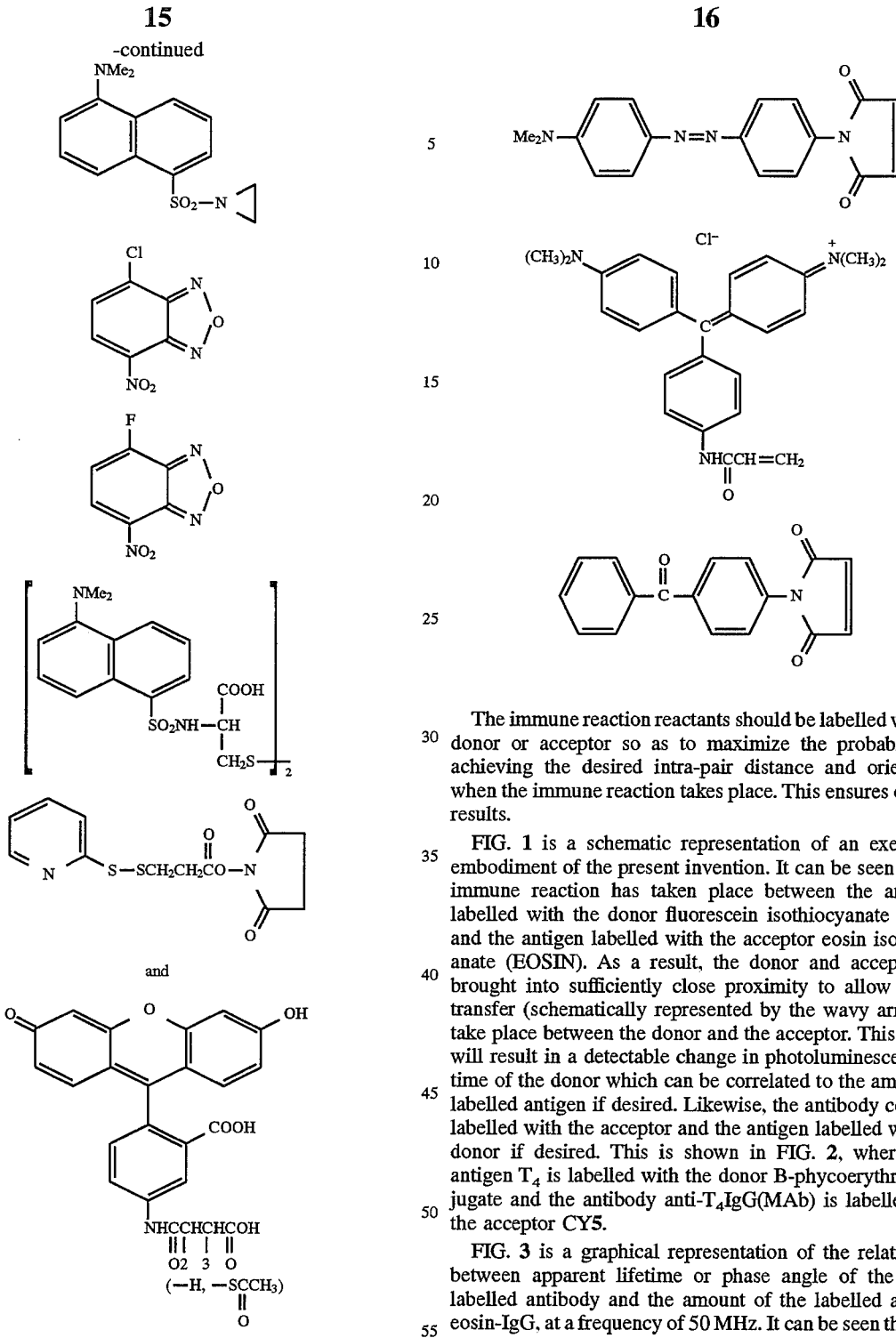

The photoluminescent energy transfer acceptors used in this invention preferably have the properties outlined above with respect to the photoluminescent energy transfer donors, with the exception that the acceptor itself need not necessarily be photoluminescent. Therefore, the classes of compounds listed above for the donors may also be used as acceptors. Additionally, compounds such as azo dyes which absorb at a suitable wavelength can be used as acceptors. The specific compounds identified above may be useful acceptors, along with eosin isothiocyanate, The immune reaction reactants should be labelled with the donor or acceptor so as to maximize the probability of achieving the desired intra-pair distance and orientation when the immune reaction takes place. This ensures optimal results.

Figure 2:
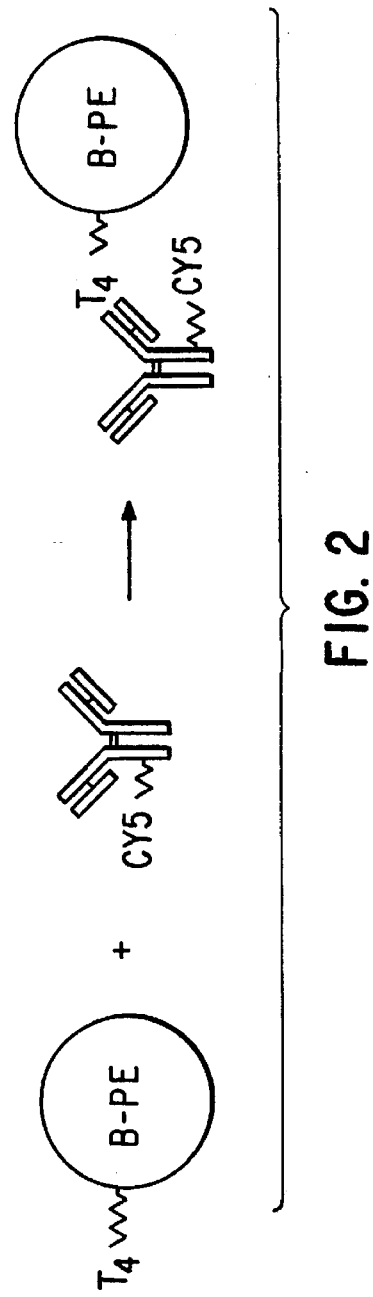

FIG. 1 is a schematic representation of an exemplary embodiment of the present invention. It can be seen that an immune reaction has taken place between the antibody labelled with the donor fluorescein isothiocyanate (FITC) and the antigen labelled with the acceptor eosin isothiocyanate (EOSIN). As a result, the donor and acceptor are brought into sufficiently close proximity to allow energy transfer (schematically represented by the wavy arrow) to take place between the donor and the acceptor. This in turn will result in a detectable change in photoluminescent lifetime of the donor which can be correlated to the amount of labelled antigen if desired. Likewise, the antibody could be labelled with the acceptor and the antigen labelled with the donor if desired. This is shown in FIG. 2, wherein the antigen $T_4$ is labelled with the donor B-phycoerythrin conjugate and the antibody anti-$T_4$IgG(MAb) is labelled with the acceptor CY5.

Figure 3:
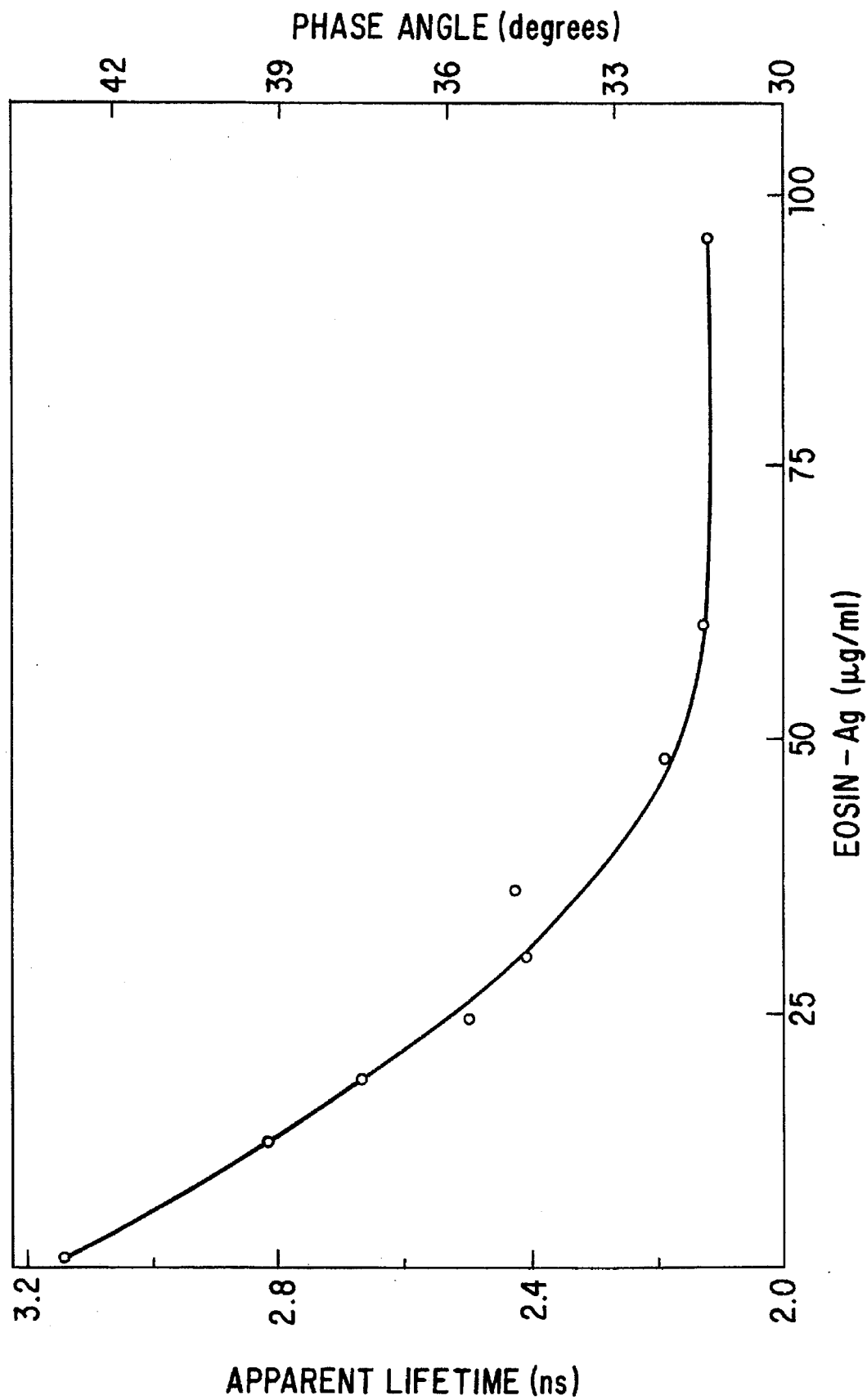
FIG. 3 is a graphical representation of apparent lifetime or phase angle v. amount of antigen for one of the immune reactions in FIG. 1.

FIG. 3 is a graphical representation of the relationship between apparent lifetime or phase angle of the FITC-labelled antibody and the amount of the labelled antigen, eosin-IgG, at a frequency of 50 MHz. It can be seen that both the measured phase angle and the derived apparent lifetime decrease with increasing amounts of the antigen (labelled with acceptor).

FIGS. 4 through 7 represent studies done using the antibody goat anti-mouse IgG (an antibody raised in goats to recognize mouse immunoglobulin G), labelled with the donor dichlorotriazinylaminofluorescein ("DTAF-GAMGG") and the antigen mouse IgG, labelled with the acceptor tetramethylrhodamine isothiocyanate ("TRITC-MIGG").

Figure 4:
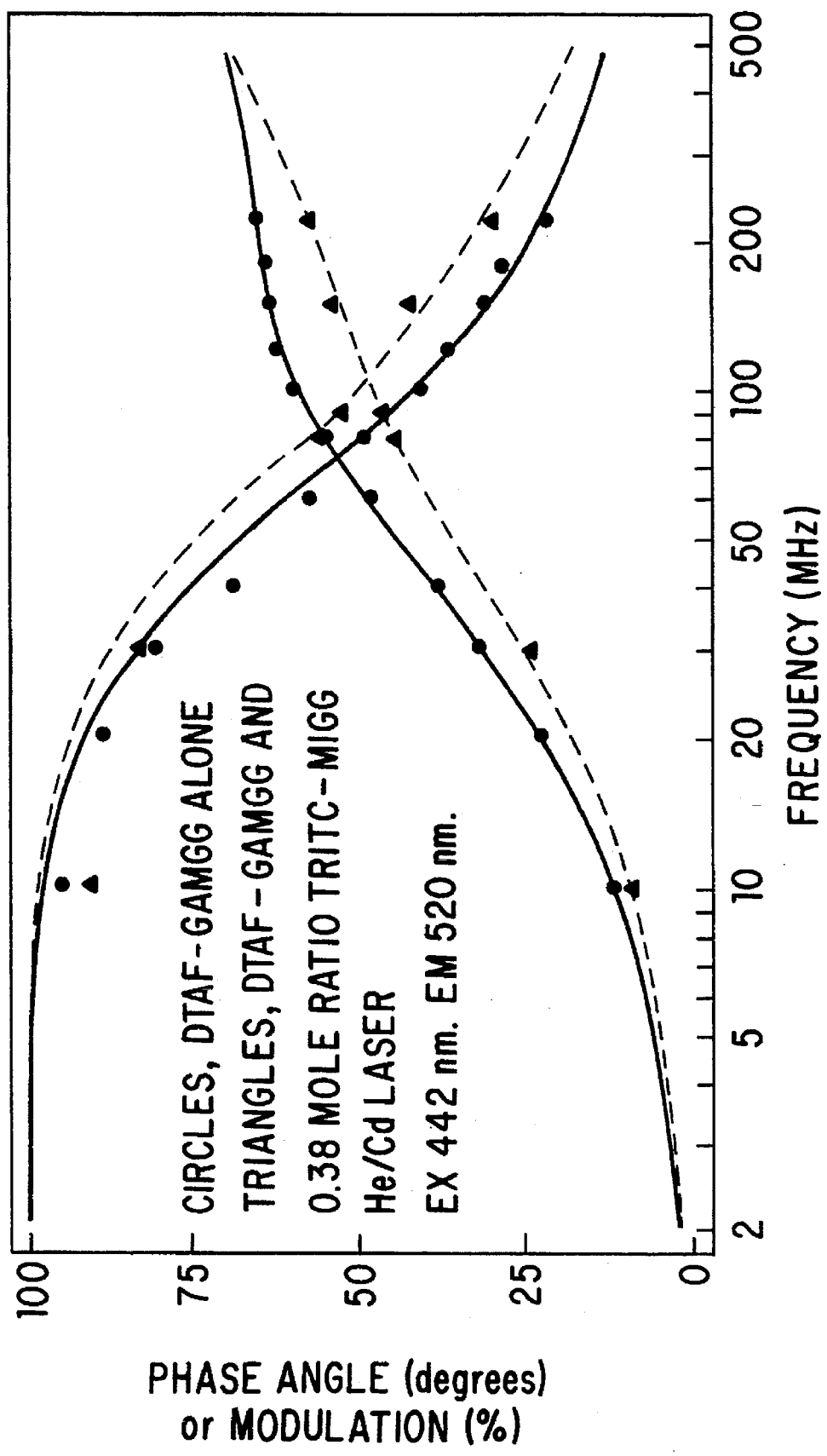
FIG. 4 is a graphical representation of phase angle and modulation v. frequency for another immune reaction in accordance with a preferred embodiment of the present invention.

FIG. 4 shows the relationship between phase angle (and modulation) and frequency for DTAF-GAMGG alone and reacted with TRITC-MIGG. The sample was excited with a He/Cd laser at an excitation wavelength of 442 nm. The emission wavelength was 520 nm. The molar ratio of TRITC-MIGG to DTAF-GAMGG was 0.38.

Figure 5:
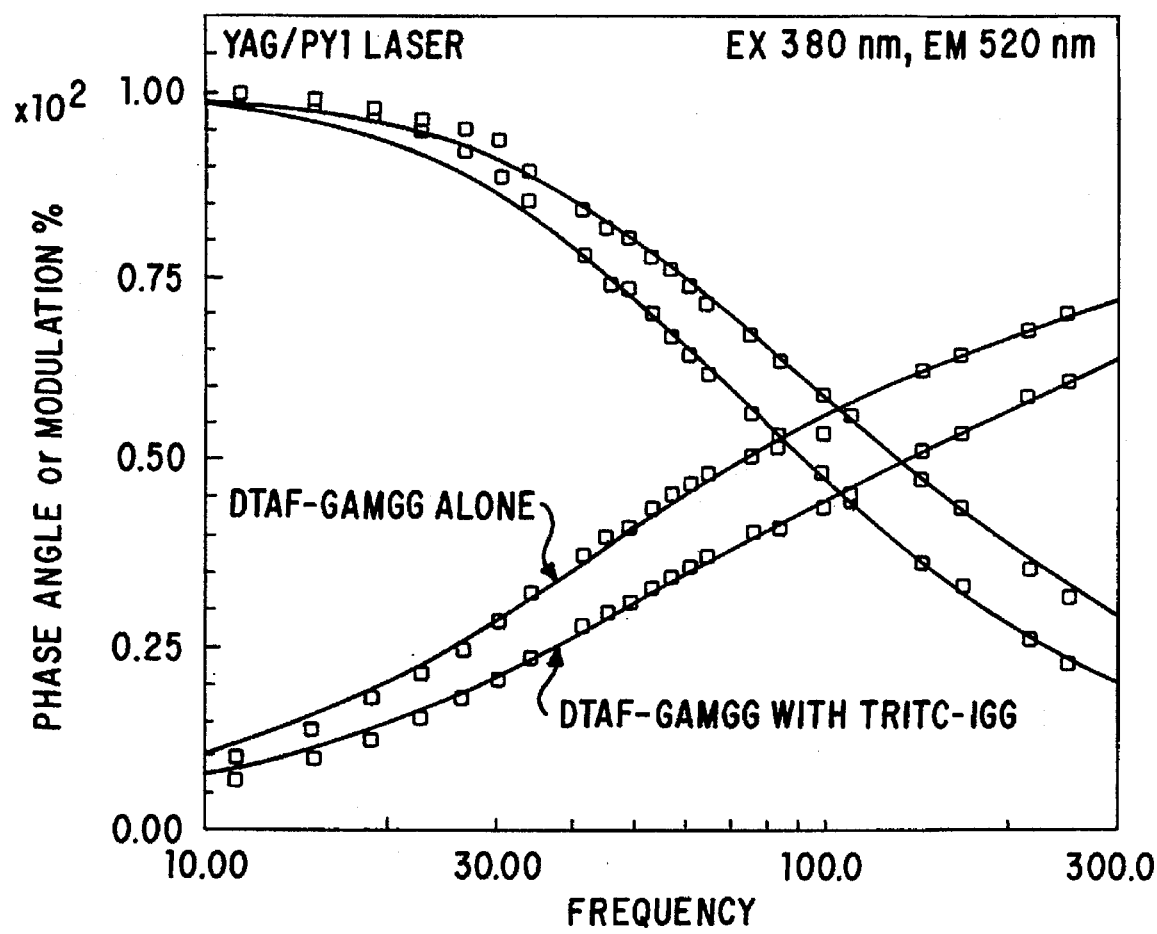
FIG. 5 is a graphical representation of phase angle and modulation v. frequency for the immune reaction in FIG. 4 using a different excitation wavelength.

FIG. 5 shows the same relationship as in FIG. 4, except that the laser was a continuous wave frequency-doubled mode-locked Nd:YAG laser synch-pumping a Pyridine 1 dye laser, whose output was frequency-doubled to provide an excitation wavelength of 380 nm.

Figure 6:
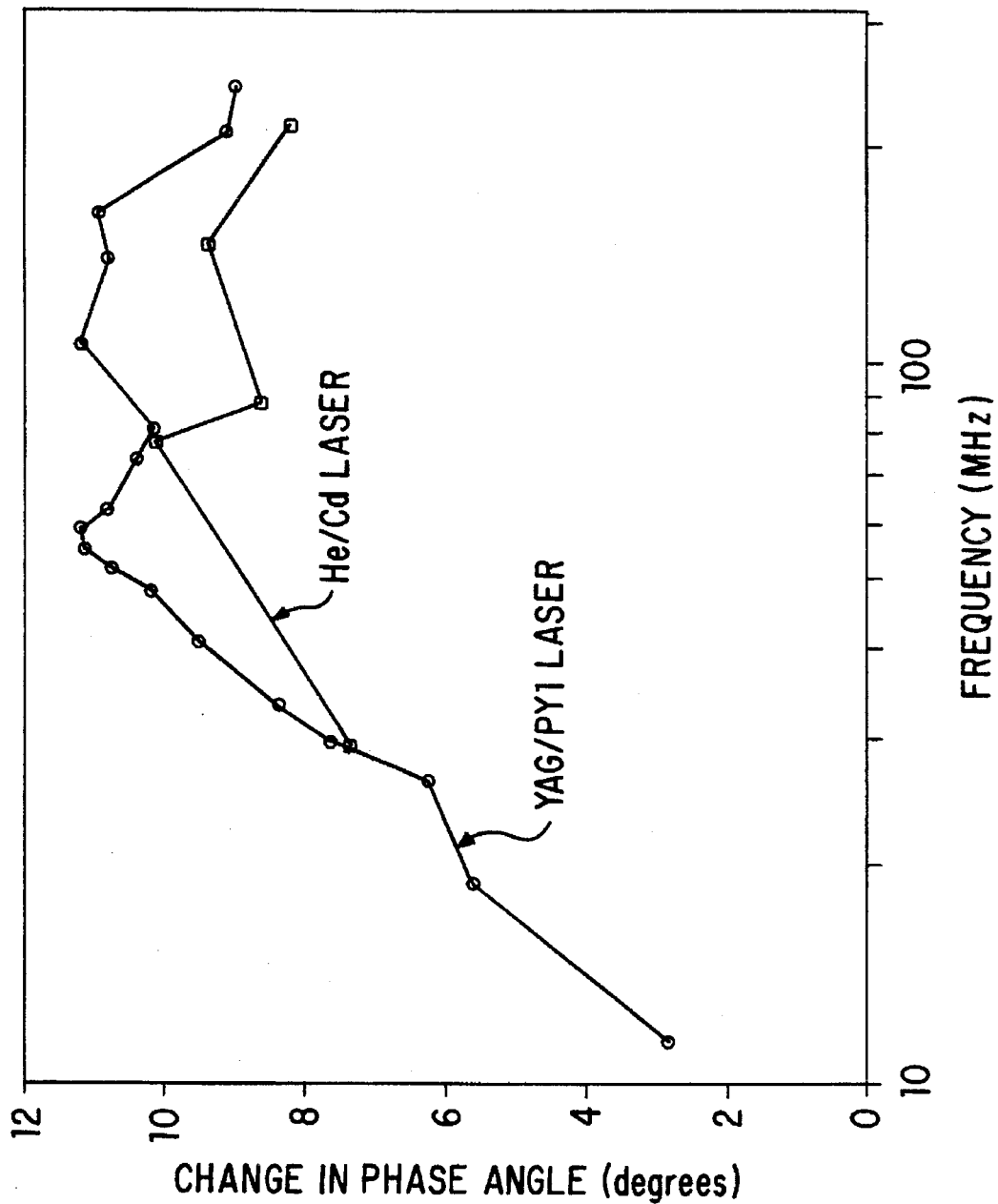
FIG. 6 is a graphical representation of phase angle v. frequency at the excitation wavelengths of FIGS. 3 and 4.

FIG. 6 shows the relationship between change in phase angle and frequency for the reactions of FIGS. 4 and 5. For both wavelengths, the change in phase angle increases with increasing frequency.

Figure 7:
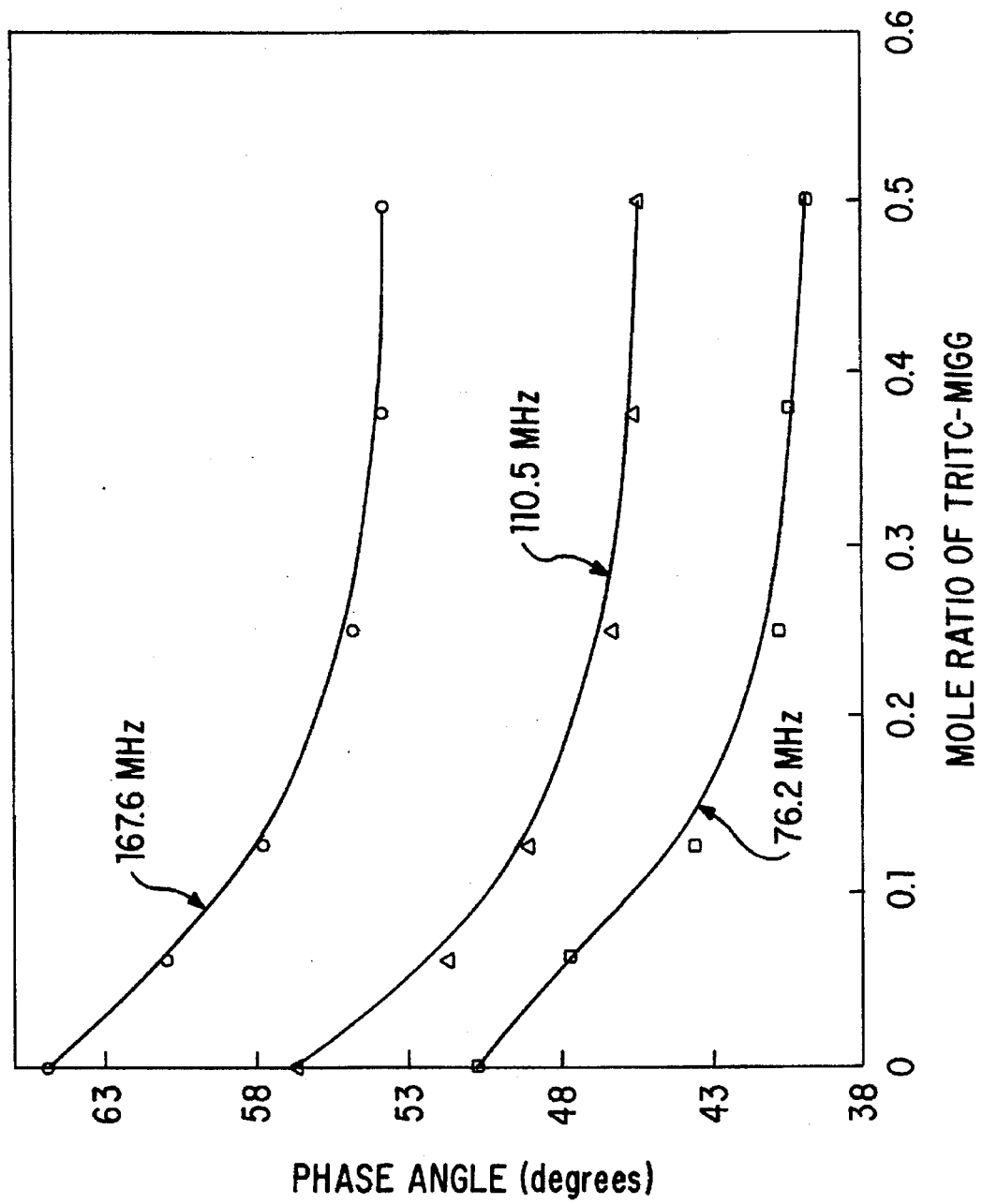
FIG. 7 is a graphical representation of phase angle v. amount of antigen at different frequencies for the immune reaction in FIG. 4.

FIG. 7 shows the relationship between phase angle and the amount of antigen for the continuous wave frequency-doubled mode-locked Nd:YAG laser synch-pumping a Pyridine 1 dye laser, modulated at different frequencies as shown. The phase angle decreases with increasing amounts of antigen.

Figure 8:
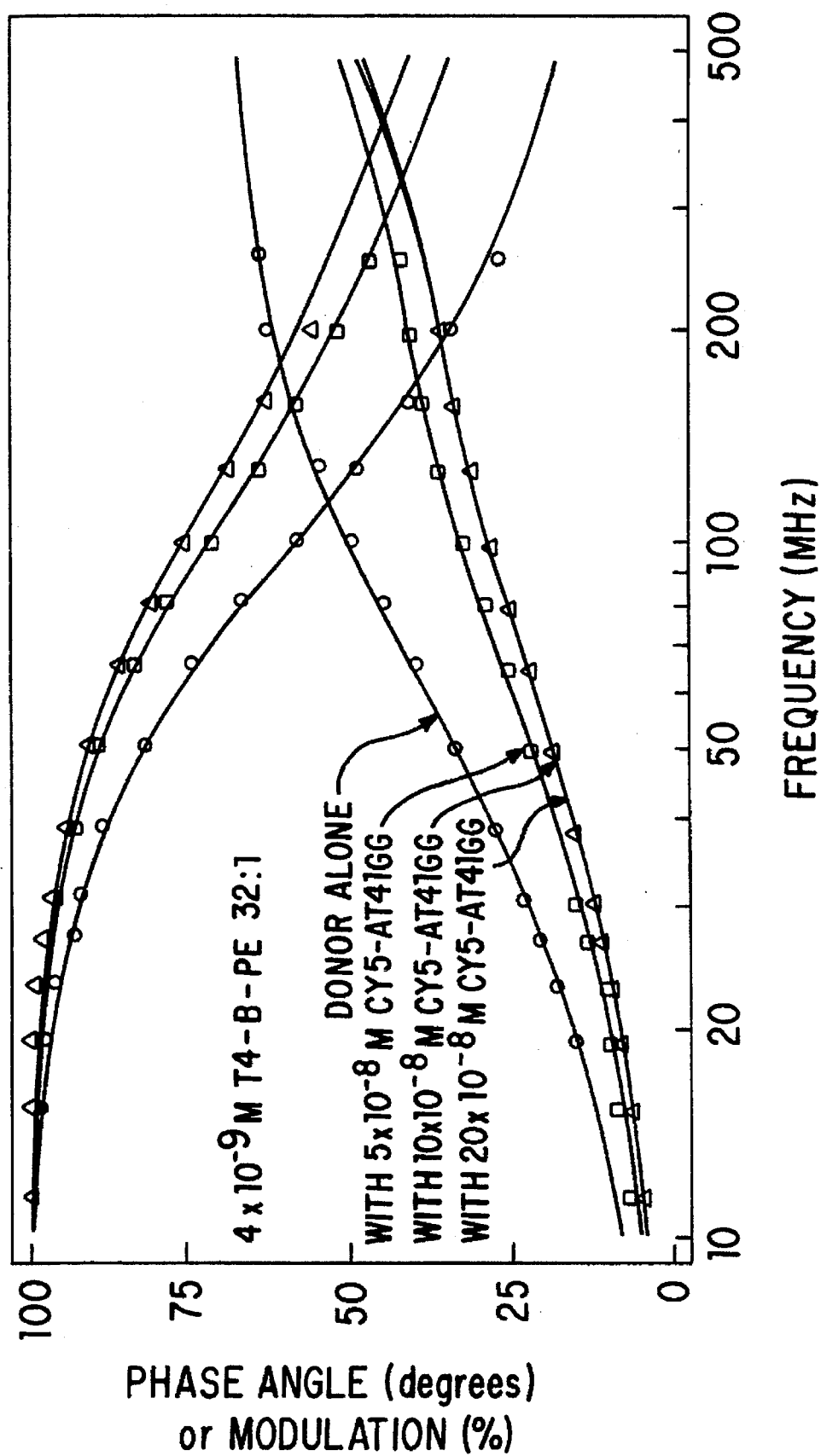
FIG. 8 is a graphical representation of change in phase angle and modulation for the immune reaction v. frequency for the reaction shown in FIG. 2.

FIG. 8 shows the relationship between phase angle or modulation and frequency for the reaction of FIG. 2, at varying concentrations of acceptor, for the YAG/R6G laser with an excitation wavelength of 560 nm. The emission wavelength was 580 nm.

Figure 9:
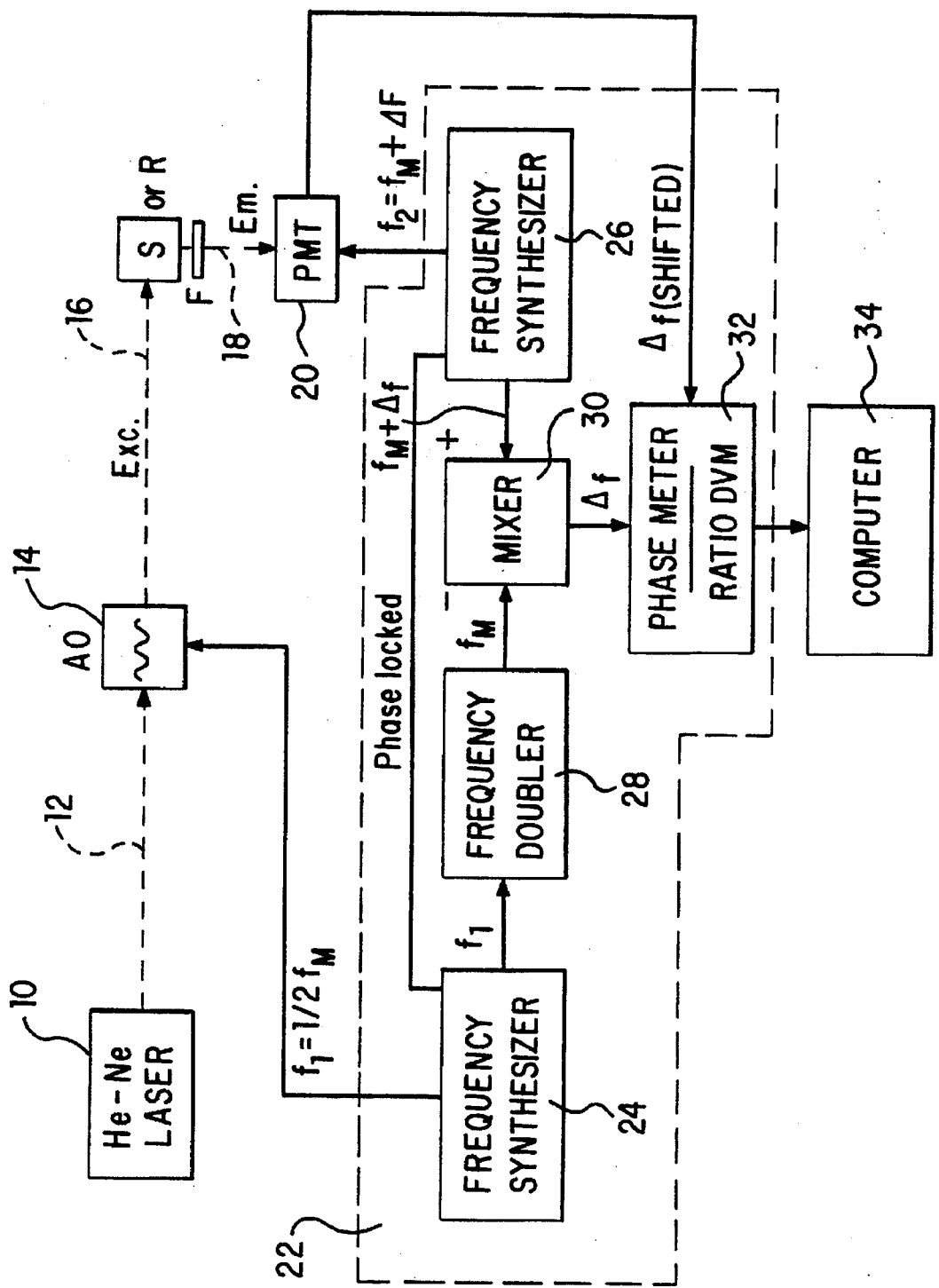
FIG. 9 is a schematic view showing a preferred embodiment of the instrumentation for use in the present invention.

One preferred embodiment of the instrumentation for use with the method of the invention is schematically shown in FIG. 9. It is to be understood, however, that any suitable instrumentation can be used.

As shown in FIG. 9, radiation source 10, in this case a helium-neon laser having an emission of 543 nm, emits excitation beam 12 which is modulated by acoustooptic modulator 14 at a frequency f1 to create sinusoidally-modulated excitation beam 16. It is to be understood that modulator 14 need not be an acoustooptic modulator, but that any suitable modulator may be used, such as an electrooptic modulator. Moreover, the modulation need not be sinusoidal, but of any desired shape. Also, the modulator need not be external, but instead the light source may be intrinsically modulated, as is known to be possible with laser diodes.

Sinusoidally-modulated excitation beam 16 irradiates sample S, which contains the labelled immune reaction reactants. The irradiated sample emits emitted beam 18 which is detected at photomultiplier tube 20. Alternatively, an avalanche photodiode may be used as the detector, particularly for infrared detection. Emitted beam 18 is amplitude modulated at the same frequency as the excitation but it is phase shifted and demodulated with respect to the excitation. It may be desirable to filter emitted beam 18 with optical filter F in order to change the effective sensitivity range of the detector.

Cross-correlation circuit 22 includes first frequency synthesizer 24 which generates frequency f1, equal to one-half of a modulation frequency fM to drive acoustooptic modulator 14. Cross-correlation circuit 22 also includes second frequency synthesizer 26 which generates a frequency f2 equal to the modulation frequency fM plus a cross-correlation frequency $\Delta f$ to drive photomultiplier tube 20. First frequency synthesizer 24 is coupled to frequency doubler 28, which directs a signal having a frequency equal to the modulation frequency fM to mixer 30. Second frequency synthesizer 26 also directs a signal having frequency f2 equal to the modulation frequency fM plus the cross-correlation frequency $\Delta f$ to mixer 30. Mixer 30 produces an output signal having a frequency equal to $\Delta f$, the difference between fM and f2.

Mixer 30 and photomultiplier tube 20 are each connected to phase meter/digital voltmeter 32. Phase meter/digital voltmeter 32 compares the output signal having a frequency $\Delta f$ received from mixer 30 and the signal having a frequency $\Delta f$(shifted) received from photomultiplier tube 20 to calculate the phase shift $\phi$ and the demodulation factor m. The phase shift $\phi$ and the demodulation factor m are then stored in computer 34.

The above is for illustrative purposes only. Modifications can be made within the scope of the invention as defined by the appended claims.

What is claimed is:

1. A competitive method of quantifying an analyte in a sample, consisting essentially of the steps of:

adding to said sample a first binding partner and a second binding partner, wherein said first binding partner competes with the analyte for binding to said second binding partner, wherein one of said first and second binding partners is labelled with a photoluminescent energy transfer donor and the other is labelled with a photoluminescent energy transfer acceptor, wherein the photoluminescent energy transfer donor and acceptor are chosen such that when the first binding partner binds to the second binding partner, the donor and the acceptor are brought into interacting proximity, producing a detectable luminescence lifetime change in the photoluminescence lifetime of the donor;

exposing the sample to an exciting amount of radiation;

detecting the resulting emission; and calculating the apparant luminescence lifetime of the donor to quantify binding of the first binding partner to the second binding partner, thereby inversely quantifying the analyte.

2. The method of claim 1, wherein the photoluminescent donor is selected from the group consisting of cyanines, oxazines, thiazines, porphyrins, phthalocyanines, fluorescent infrared-emitting polynuclear aromatic hydrocarbons, phycobiliproteins, sulfonyl chlorides, carbodiimides, haloacetyl derivatives, squaraines and organo-metallic complexes.

3. The method of claim 1, wherein the photoluminescent acceptor is selected from the group consisting of cyanines, oxazines, thiazines, porphyrins, phthalocyanines, polynuclear aromatic hydrocarbons, phycobiliproteins, squaraines, organo-metallic complexes, carbodiimides, sulfonyl chlorides, haloacetyls, and azo dyes.

4. The method of claim 1, wherein the apparent lifetime is calculated using phase-modulation fluorometry.

5. The method of claim 1, wherein the apparent lifetime is calculated using time-resolved fluorometry.

6. The method of claim 2, wherein the photoluminescent donor is selected from the group consisting of: fluoresceinisothiocyanate, dichlorotriazinylaminofluorescein, 1,3- bis-(2-dialkylamino-5-thienyl)-substituted squaraines, and compounds having the following structural formulas:

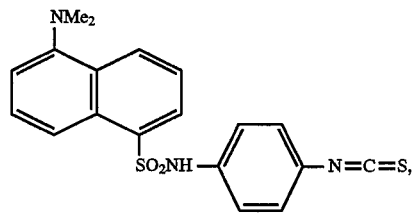

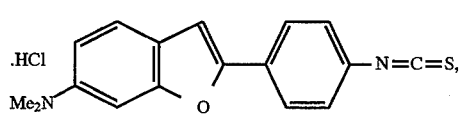
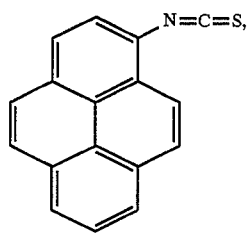
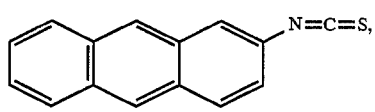
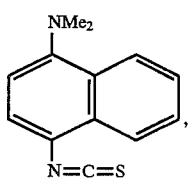
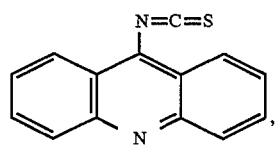
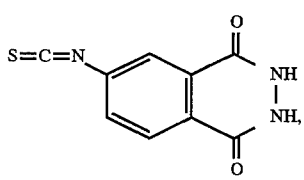
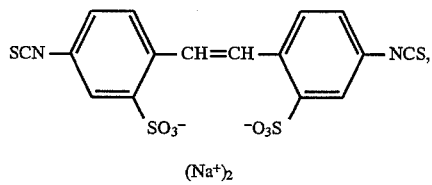
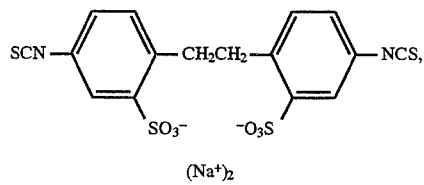
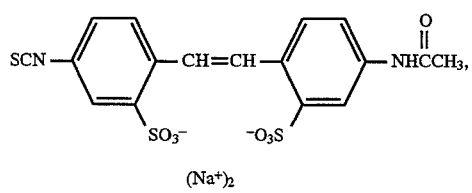
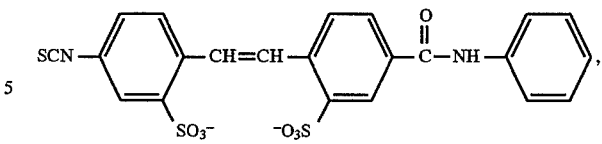
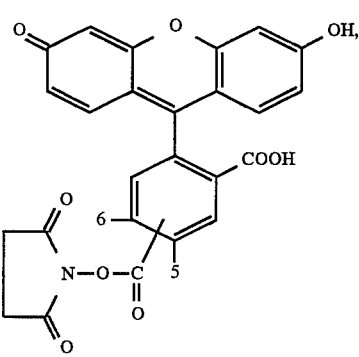
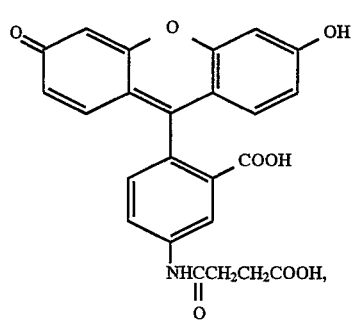
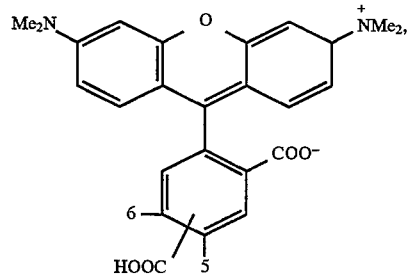
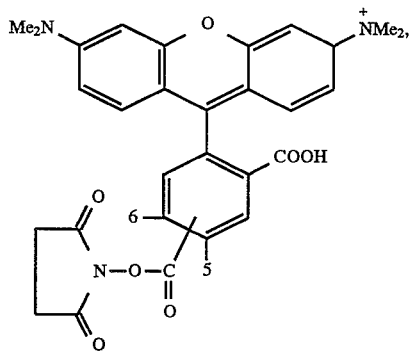

21
-continued
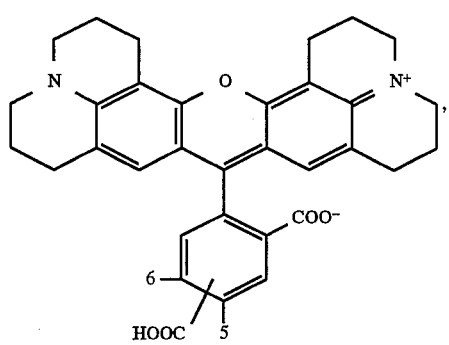
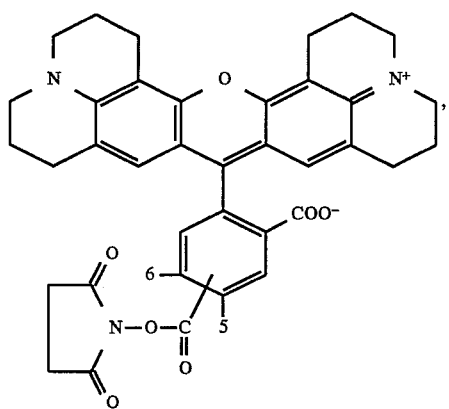
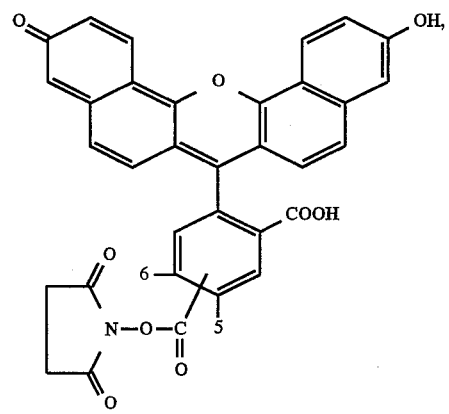
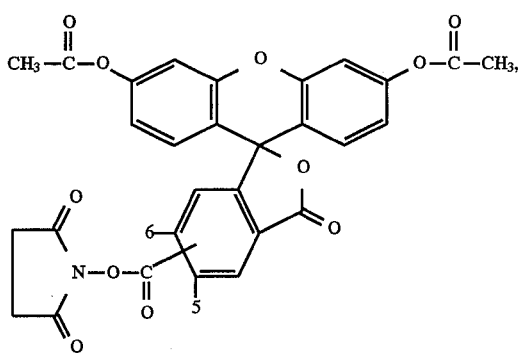
22
-continued
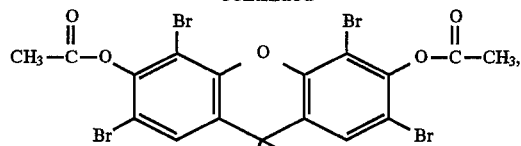
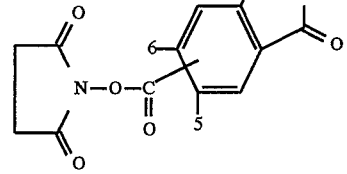
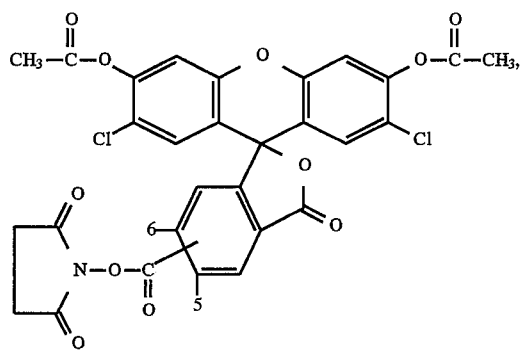
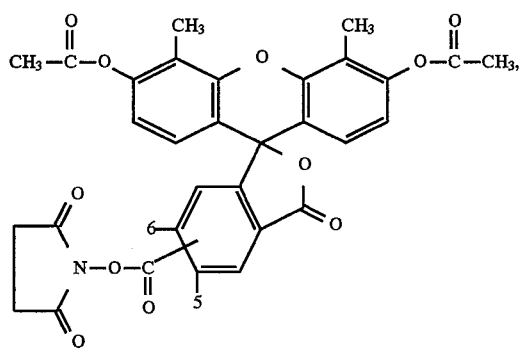
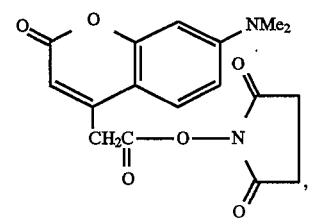
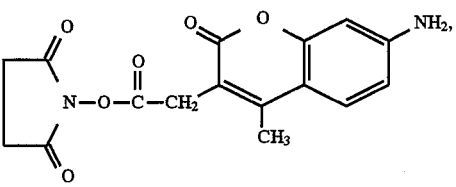
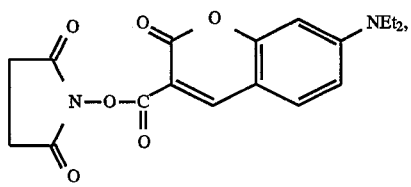

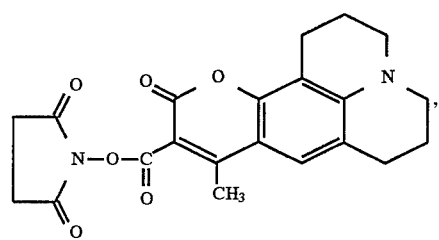
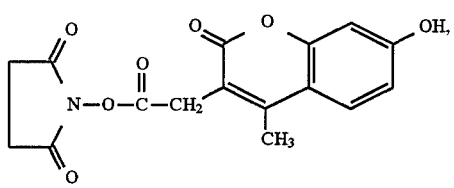
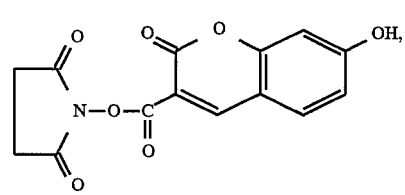
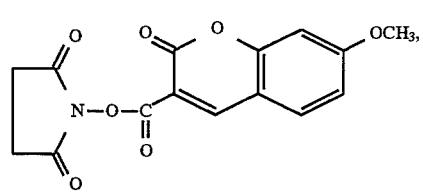
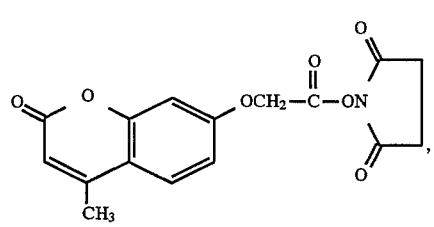
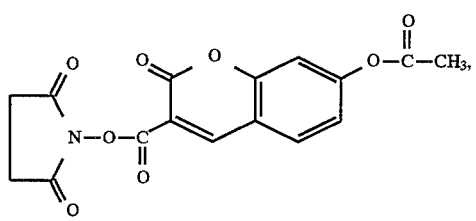
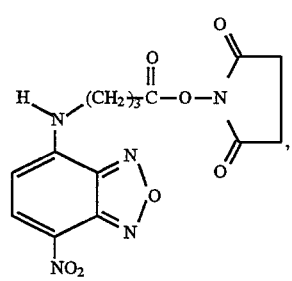
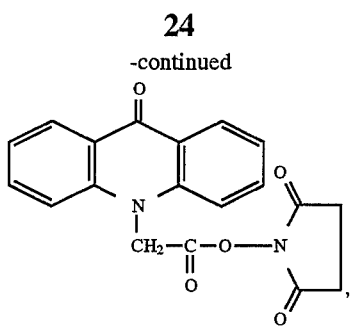
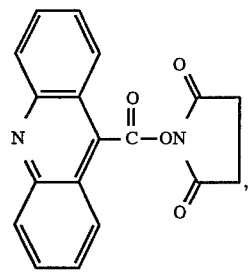
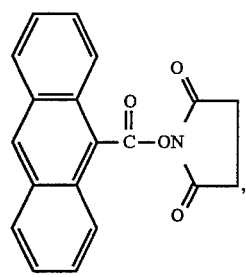
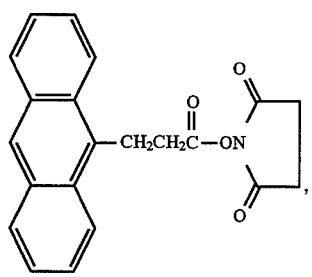
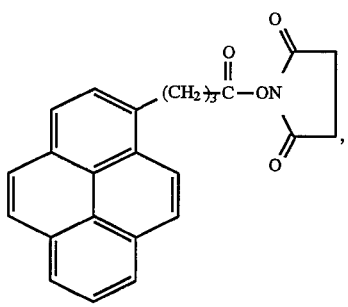
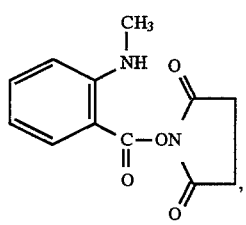

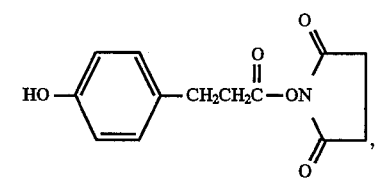
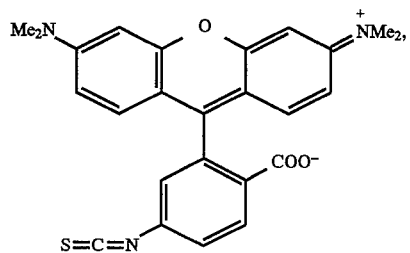
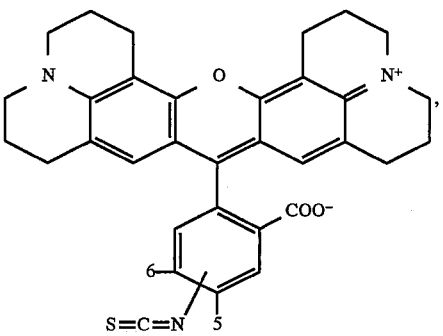
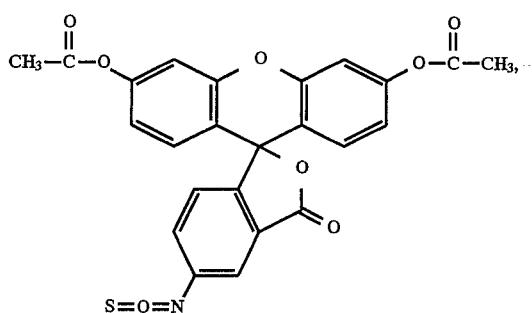
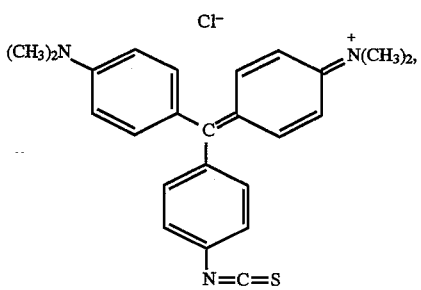
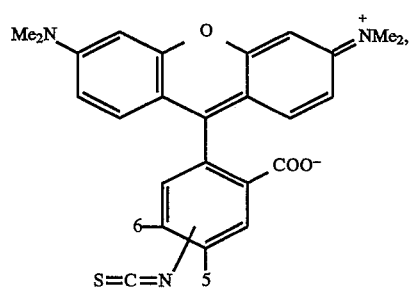
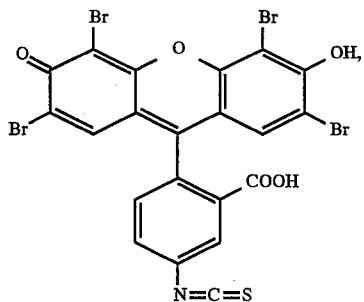
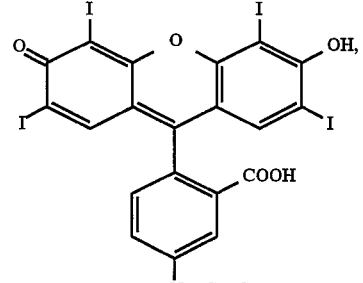
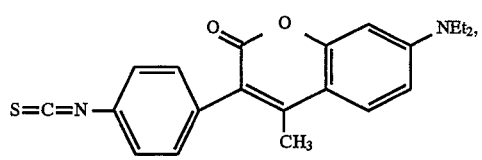

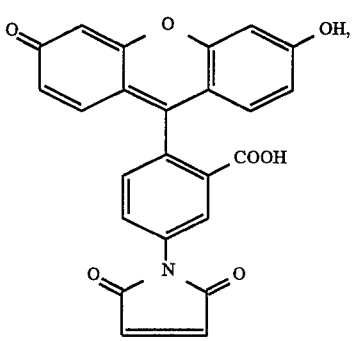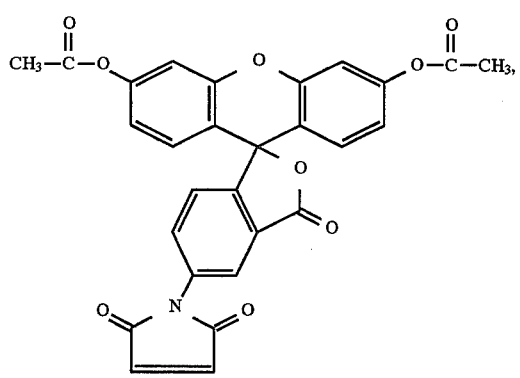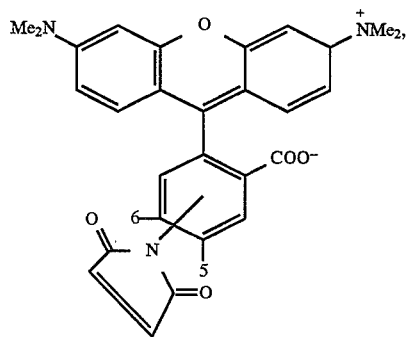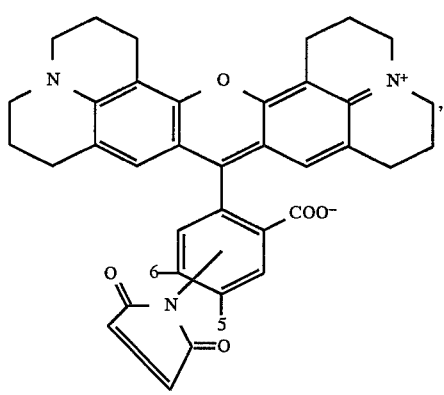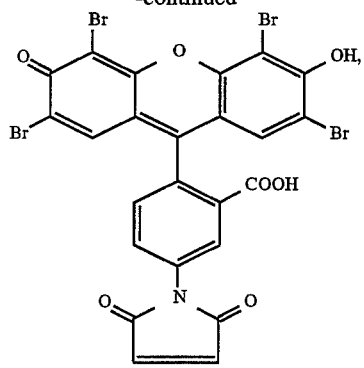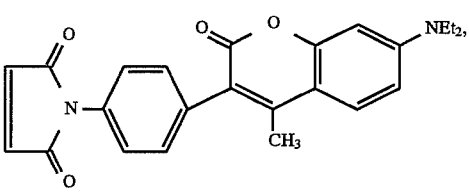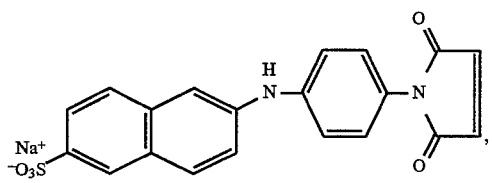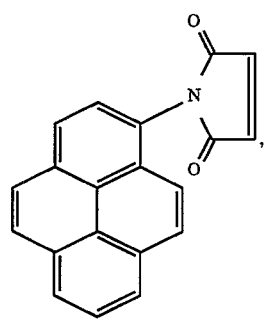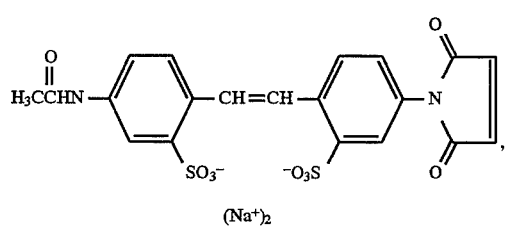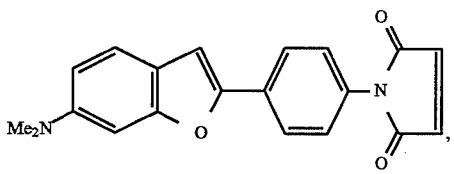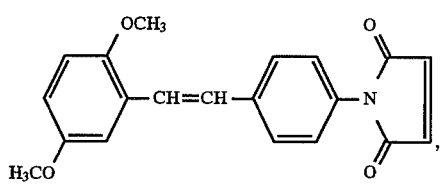

29
-continued
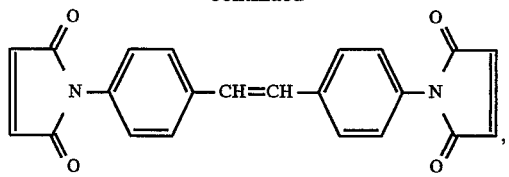
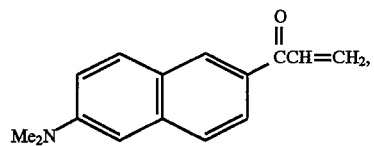
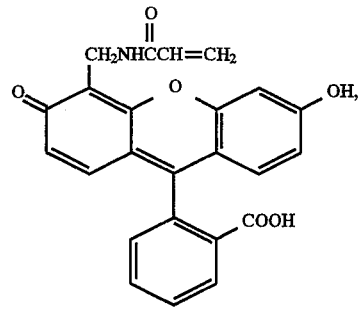
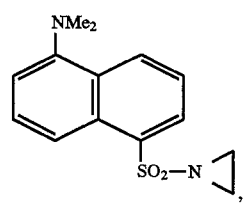
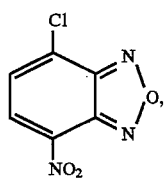
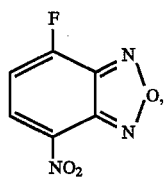
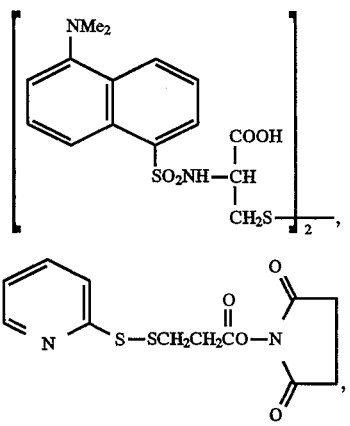
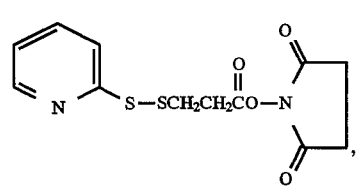
and
30
-continued
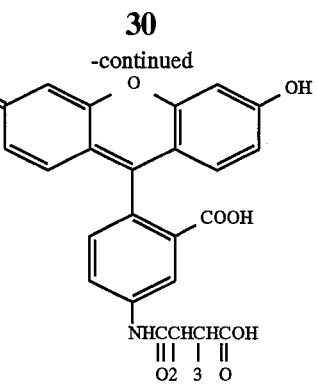
(—H, —SCCH₃).
       ‖
       O
7. The method of claim 3, wherein the photoluminescent acceptor is selected from the group consisting of: eosin isothiocyanate, tetramethylrhodamine isothiocyanate, 1,3-bis-(2-dialkylamino-5-thienyl)-substituted squaraines, and compounds having the following structural formulas:
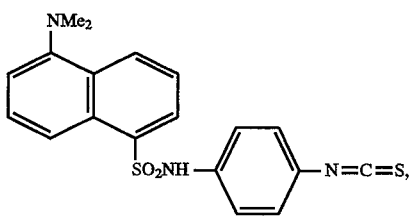
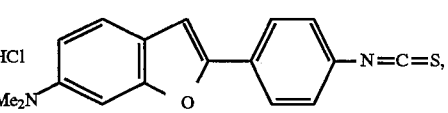
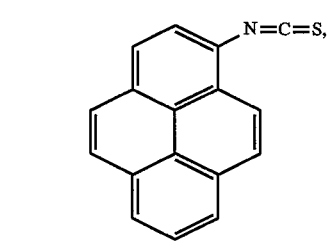
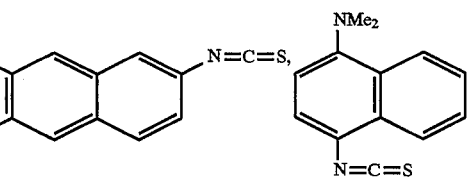
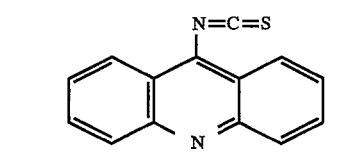
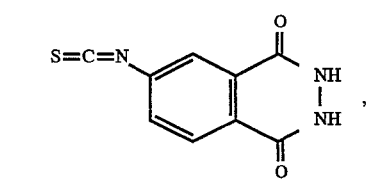

-continued
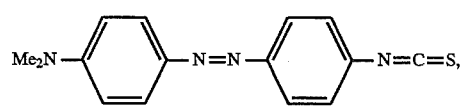
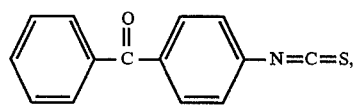
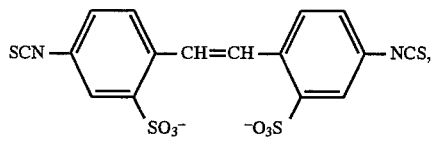
$(Na^+)_2$
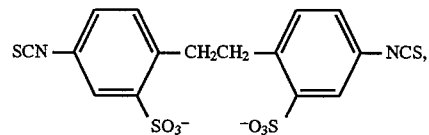
$(Na^+)_2$
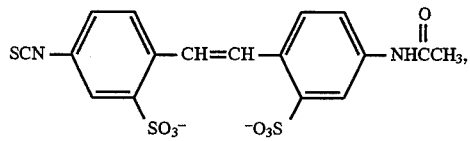
$(Na^+)_2$
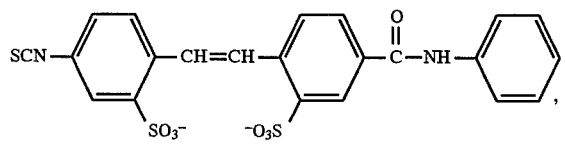
$(Na^+)_2$
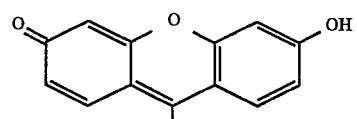
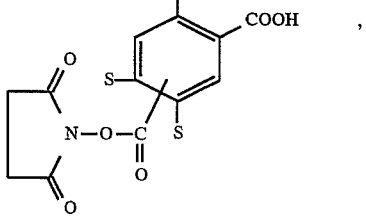
-continued
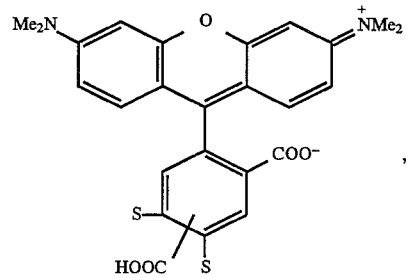
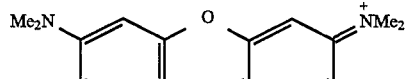
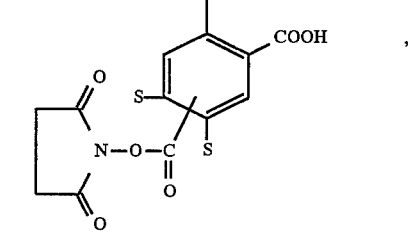
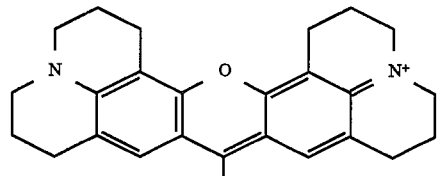
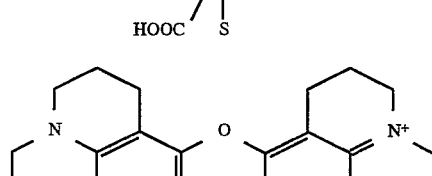
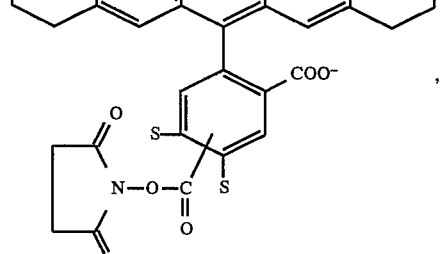
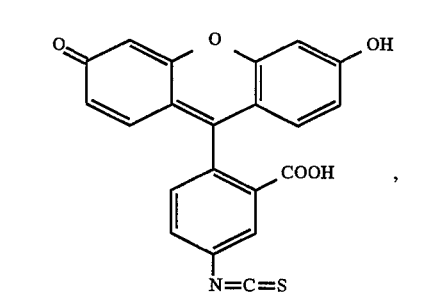
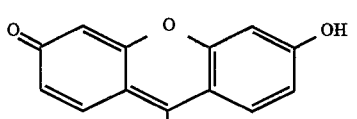
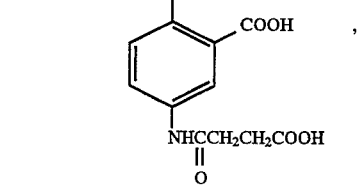

33
-continued
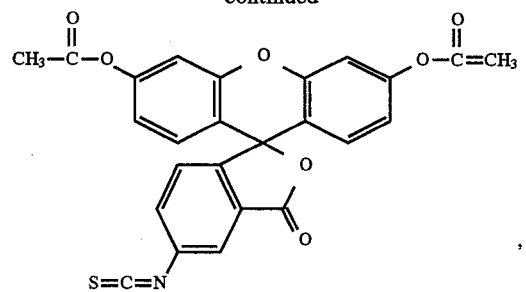
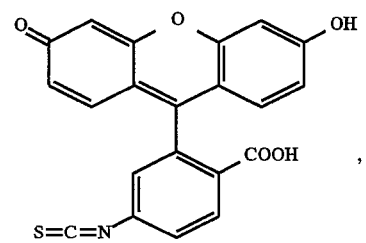
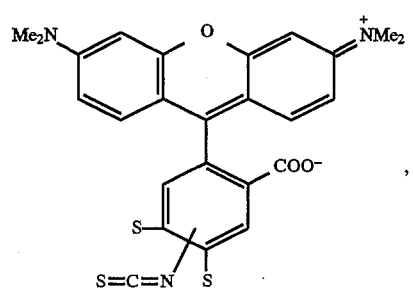,
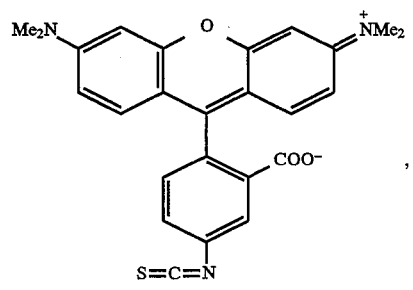,
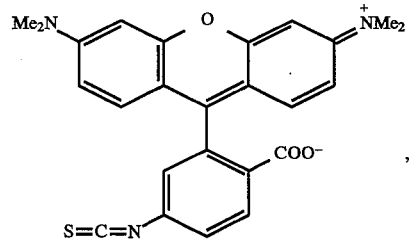,
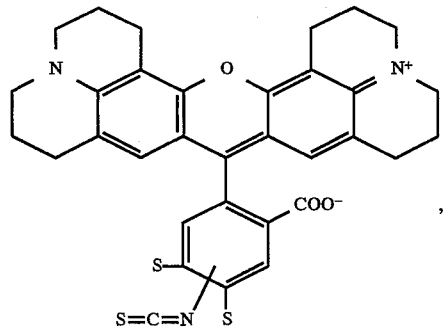,
34
-continued
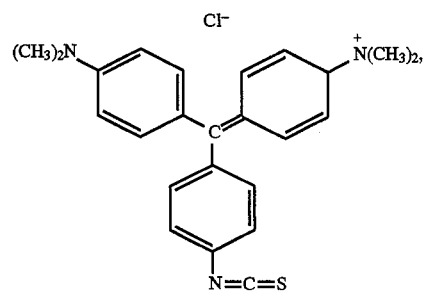
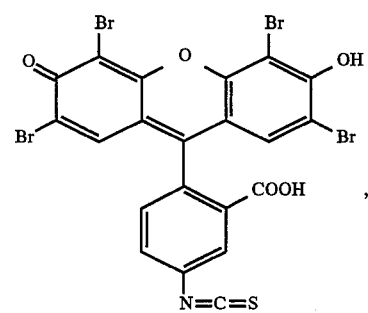,
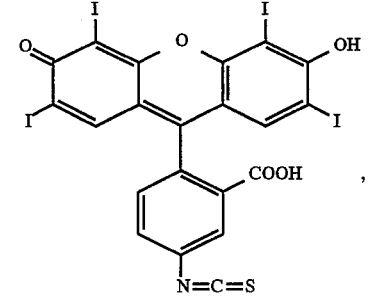,
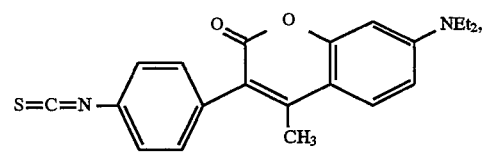,
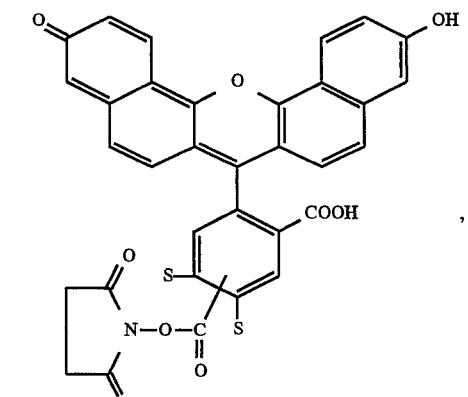,

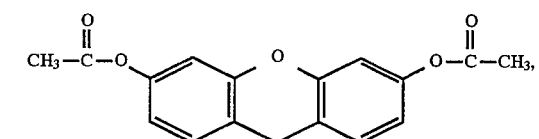
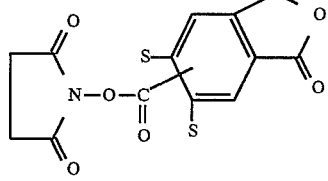
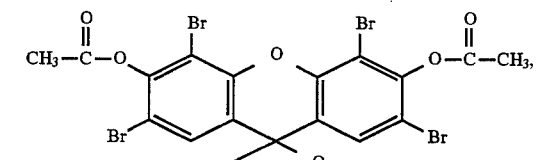
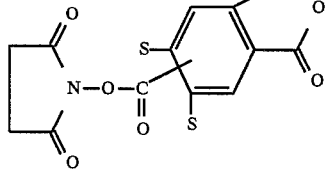
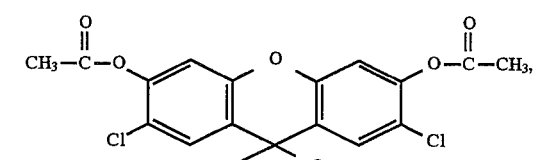
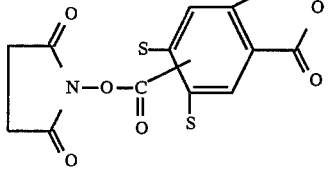
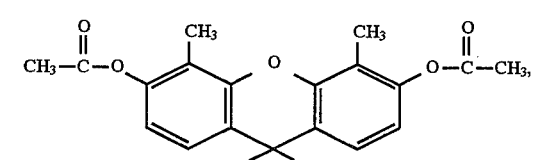
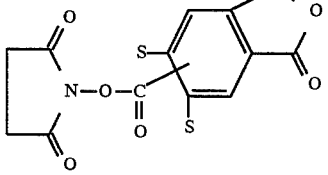
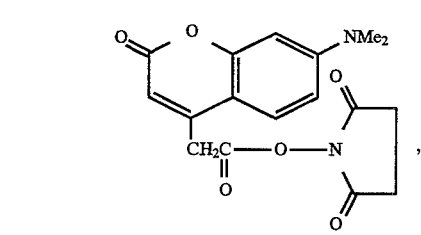
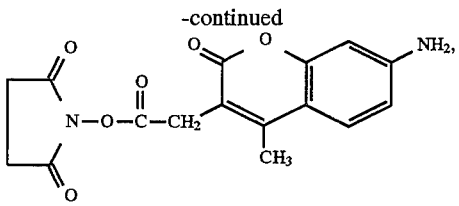
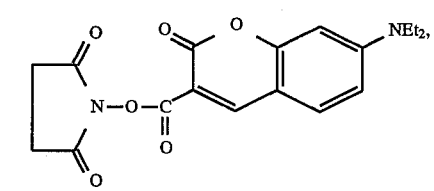
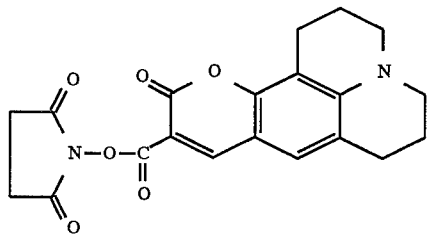
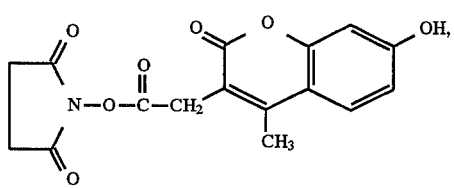
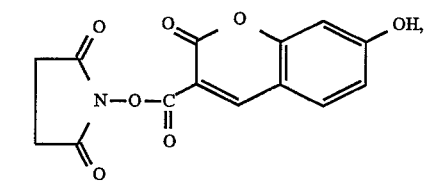
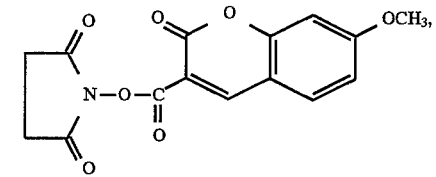
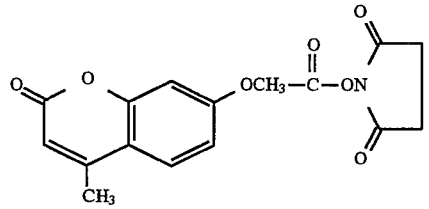
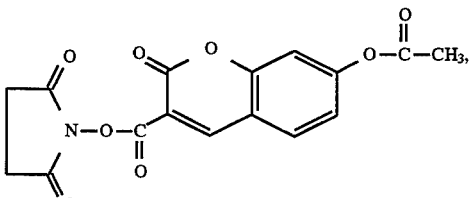

37
-continued
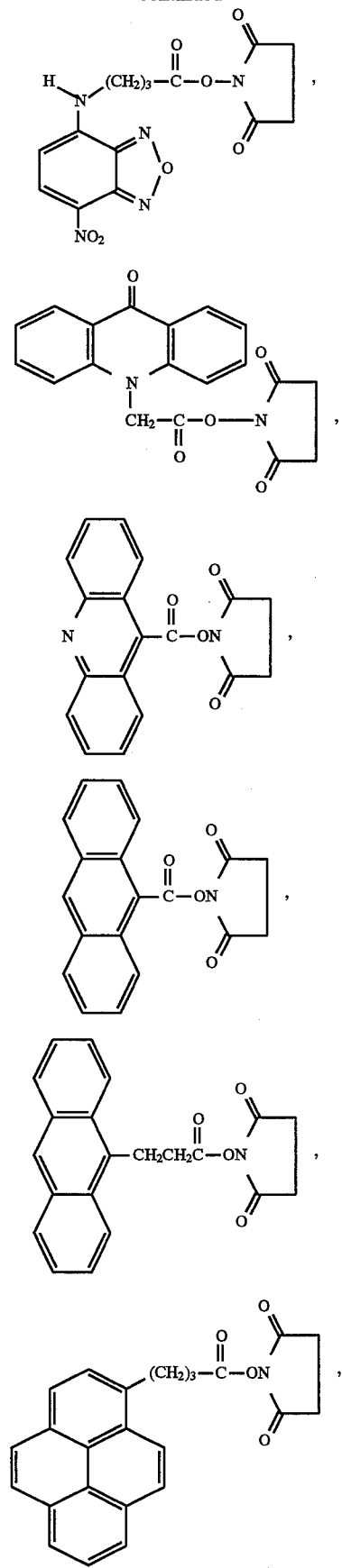
38
-continued
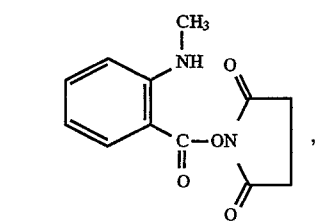
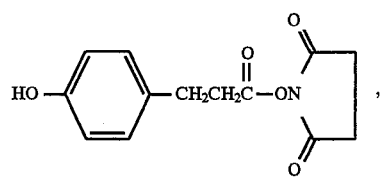
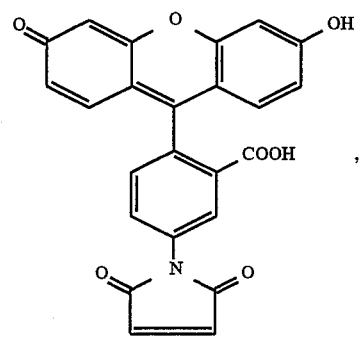
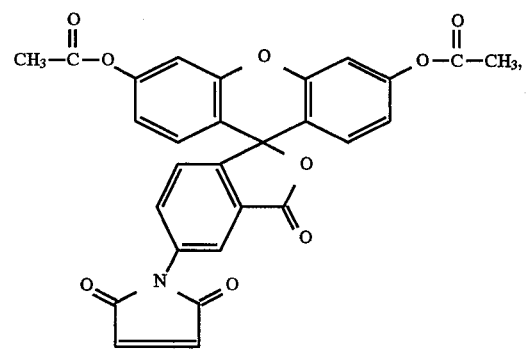
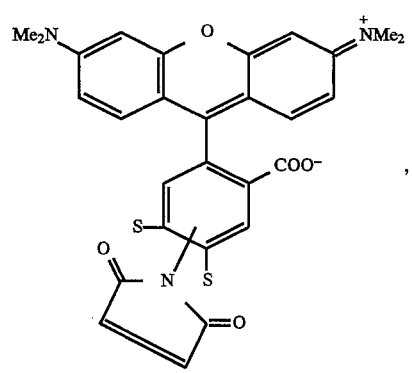

39
-continued
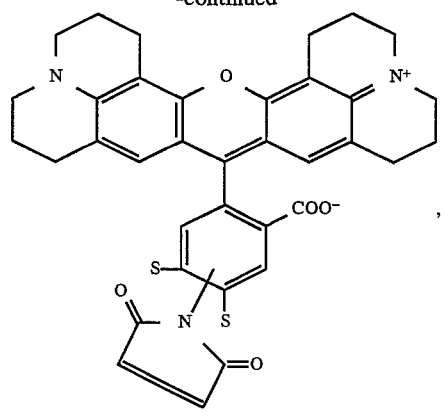
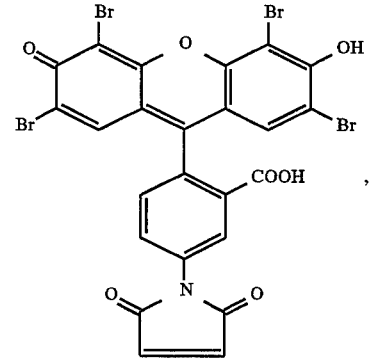
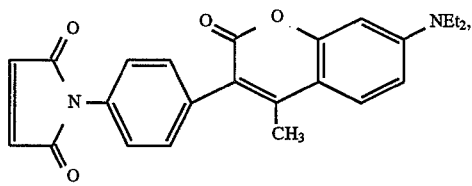
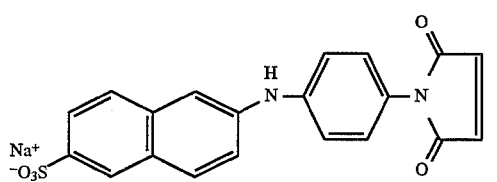
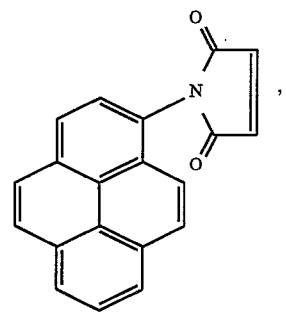
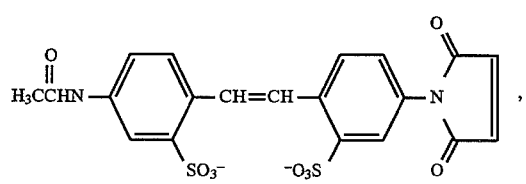
40
-continued
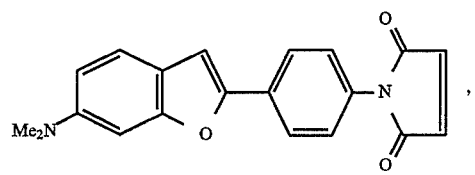
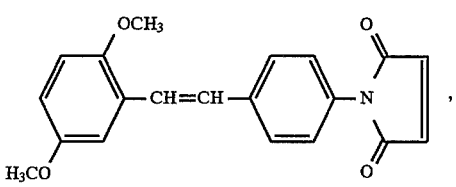
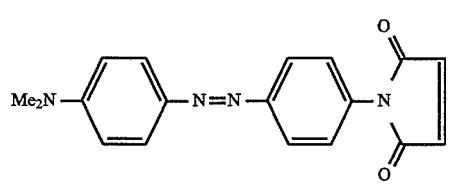
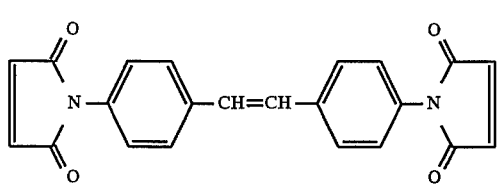
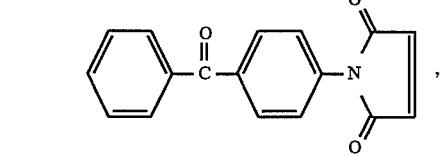
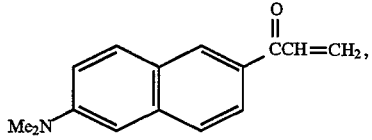
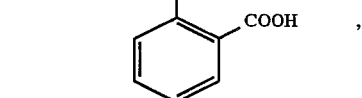

-continued

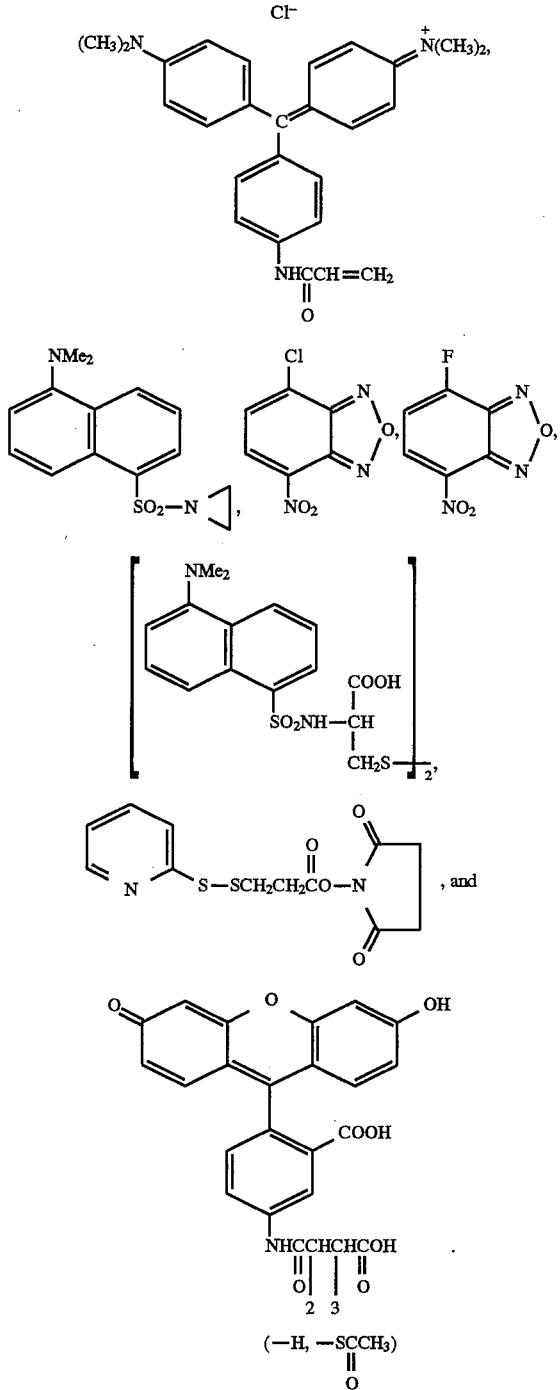

8. The method of claim 1, wherein the sample is formed in vitro.

9. The method of claim 1, wherein the sample is excited using a Ti-sapphire laser, a laser diode or a continuous wave frequency-double mode-locked argon ion or Nd:YAG laser synch-pumping a dye laser.

10. The method of claim 9, wherein the sample is excited at a wavelength of 380 nm.

11. The method of claim 1, wherein the lifetime is about 5 ns.

12. The method of claim 1, wherein the sample is excited with a HeNe laser or laser diode.

13. The method of claim 1, wherein the donor or acceptor is selected from the group consisting of succinimidyl esters of:

5- or 6- carboxyfluorescein; 5- or 6- carboxytetra-methylrhodamine; and 7-amino-4-methylcoumarin-3-acetic acid.

14. The method of claim 1, wherein the radiation is modulated light or pulsed light.

15. The method of claim 14, wherein the sample is excited with sinusoidally modulated light or square wave light.

16. The method of claim 14, wherein the sample is excited using a helium-cadmium laser.

17. The method of claim 16, wherein the sample is excited at a wavelength of 442 nm.

18. The method of claim 1, wherein the donor has a lifetime of about 0.1 ns to 400 ns.

19. The method of claim 4, wherein there is a phase angle difference of about 45 degrees.

20. A competitive method of quantifying an analyte in a sample, comprising the steps of:

adding to said sample a first binding partner and a second binding partner, wherein said first binding partner competes with the analyte for binding to said second binding partner, wherein one of said first and second binding partners is labelled with a photoluminescent energy transfer donor and the other is labelled with a photoluminescent energy transfer acceptor, wherein the photoluminescent energy transfer donor and acceptor are chosen such that when the first binding partner binds to the second binding partner, the donor and the acceptor are brought into interacting proximity, producing a detectable luminescence lifetime change in the photoluminescence lifetime of the donor;

exposing the sample to an exciting amount of radiation;

detecting the resulting emission; and calculation the apparent luminescence lifetime of the donor without the use of a fluorescence intensity measurement to quantify binding of the first binding partner to the second binding partner, thereby inversely quantifying the analyte.

21. A sandwich method of quantifying an analyte in a sample, consisting essentially of the steps of:

adding to said sample a first binding partner and a second binding partner, wherein said first binding partner and said second binding partner bind to the analyte to form an immune complex, wherein one of said first and second binding partners is labelled with a photoluminescent energy transfer donor and the other is labelled with a photoluminescent energy transfer acceptor, wherein the photoluminescent energy transfer donor and acceptor are chosen such that when the immune complex is formed, the donor and the acceptor are brought into interacting proximity, producing a detectable luminescence lifetime change in the photoluminescence lifetime of the donor;

exposing the sample to an exciting amount of radiation;

detecting the resulting emission; and calculating the apparant luminescence lifetime of the donor without the use of a fluorescence intensity measurement to quantify the immune complex, thereby quantifying the analyte.

22. A sandwich method of quantifying an analyte in a sample, consisting essentially of the steps of:

adding to said sample a first binding partner and a second binding partner, wherein said first binding partner and said second binding partner bind to the analyte to form an immune complex, wherein one of said first and second binding partners is labelled with a photoluminescent energy transfer donor and the other is labelled with a photoluminescent energy transfer acceptor, wherein the photoluminescent energy transfer donor and acceptor are chosen such that when said immune complex is formed, the donor and the acceptor are brought into interacting proximity, producing a detectable luminescence lifetime change in the photoluminescence lifetime of the donor;

exposing the sample to an exciting amount of radiation;

detecting the resulting emission; and calculating the apparent luminescence lifetime of the donor without the use of a fluorescence intensity measurement to quantify the immune complex, thereby quantifying the analyte.

* * * * *